(12) United States Patent
Kolls et al.

(10) Patent No.: US 7,704,503 B2
(45) Date of Patent: Apr. 27, 2010

(54) USE OF IL-17F IN DIAGNOSIS AND THERAPY OF AIRWAY INFLAMMATION

(75) Inventors: Jay K. Kolls, Sewickley, PA (US); Florencia Marine McAllister, Pittsburgh, PA (US); Beatriz M. Carreno, Clayton, MO (US); Samuel J. Goldman, Acton, MA (US)

(73) Assignees: Wyeth LLC, Madison, NJ (US); University of Pittsburgh of the Commonwealth System of Higher Education, Pittsburgh, PA (US)

( * ) Notice: Subject to any disclaimer, the term of this patent is extended or adjusted under 35 U.S.C. 154(b) by 143 days.

(21) Appl. No.: 11/354,609

(22) Filed: Feb. 14, 2006

(65) Prior Publication Data
US 2006/0257930 A1     Nov. 16, 2006

Related U.S. Application Data

(60) Provisional application No. 60/653,186, filed on Feb. 14, 2005.

(51) Int. Cl.
| A61K 39/395 | (2006.01) |
| A61K 39/38 | (2006.01) |
| A61K 45/00 | (2006.01) |
| G01N 33/53 | (2006.01) |
| C12Q 1/68 | (2006.01) |
| A01N 43/04 | (2006.01) |

(52) U.S. Cl. ............... 424/145.1; 424/184.1; 424/85.2; 435/7.1; 435/6; 514/44 R

(58) Field of Classification Search ...................... None
See application file for complete search history.

(56) References Cited

U.S. PATENT DOCUMENTS

| 4,235,871 A | 11/1980 | Papahadjopoulos et al. .... 424/19 |
| 4,501,728 A | 2/1985 | Geno et al. .................... 424/38 |
| 4,737,323 A | 4/1988 | Martin et al. ................. 264/4.3 |
| 4,816,567 A | 3/1989 | Cabilly et al. ................ 530/387 |
| 4,837,028 A | 6/1989 | Allen ......................... 424/1.21 |
| 5,225,538 A | 7/1993 | Capon et al. ............... 530/387.3 |
| 5,225,539 A | 7/1993 | Winter ...................... 530/387.3 |
| 5,399,677 A | 3/1995 | Wolfman et al. ............ 536/23.5 |
| 5,428,130 A | 6/1995 | Capon et al. ................ 530/350 |
| 5,455,165 A | 10/1995 | Capon et al. ................ 435/64.7 |
| 5,514,582 A | 5/1996 | Capon et al. ............... 435/252.3 |
| 5,516,964 A | 5/1996 | Umansky et al. ............ 585/751 |
| 5,585,089 A | 12/1996 | Queen et al. ................ 424/133.1 |
| 5,624,821 A | 4/1997 | Winter et al. ............... 435/69.6 |
| 5,648,260 A | 7/1997 | Winter et al. ............... 435/252.3 |
| 5,693,761 A | 12/1997 | Queen et al. ................ 536/23.53 |
| 5,693,762 A | 12/1997 | Queen et al. ............... 530/387.3 |
| 5,707,829 A | 1/1998 | Jacobs et al. ................ 435/69.1 |
| 5,714,147 A | 2/1998 | Capon et al. ............... 424/178.1 |
| 5,830,877 A | 11/1998 | Carson et al. ................... 514/44 |
| 6,043,344 A | 3/2000 | Jacobs et al. ................ 530/351 |
| 6,072,037 A | 6/2000 | Yao et al. ................ 530/388.22 |
| 6,074,849 A | 6/2000 | Jacobs et al. ............... 435/69.5 |
| 6,258,562 B1 | 7/2001 | Salfeld et al. ............... 435/69.6 |
| 6,350,892 B1 | 2/2002 | Banville et al. .............. 556/436 |
| 6,506,559 B1 | 1/2003 | Fire et al. ....................... 435/6 |
| 6,902,735 B1 | 6/2005 | Jacobs et al. .............. 424/145.1 |
| 2002/0136724 A1 | 9/2002 | Mohler et al. ............. 424/145.1 |
| 2003/0118592 A1 | 6/2003 | Ledbetter et al. .......... 424/178.1 |
| 2003/0133939 A1 | 7/2003 | Ledbetter et al. .......... 424/178.1 |
| 2004/0058445 A1 | 3/2004 | Ledbetter et al. ............. 435/372 |
| 2004/0043397 A1 | 4/2004 | Chen et al. ................... 435/500 |
| 2004/0175790 A1 | 9/2004 | Shi et al. .................... 435/69.1 |
| 2005/0136049 A1 | 6/2005 | Ledbetter et al. .......... 424/132.1 |
| 2005/0175614 A1 | 8/2005 | Ledbetter et al. .......... 424/145.1 |
| 2005/0180970 A1 | 8/2005 | Ledbetter et al. .......... 424/143.1 |
| 2005/0186216 A1 | 8/2005 | Ledbetter et al. .......... 424/155.1 |
| 2005/0202012 A1 | 9/2005 | Ledbetter et al. .......... 424/144.1 |
| 2005/0202023 A1 | 9/2005 | Ledbetter et al. .......... 424/155.1 |
| 2005/0202028 A1 | 9/2005 | Ledbetter et al. .......... 424/178.1 |
| 2005/0202534 A1 | 9/2005 | Ledbetter et al. ............ 435/69.1 |
| 2005/0238646 A1 | 10/2005 | Ledbetter et al. .......... 424/144.1 |
| 2005/0244874 A1* | 11/2005 | Kastelein et al. ................. 435/6 |
| 2006/0002925 A1* | 1/2006 | Presnell et al. ............ 424/143.1 |
| 2006/0039902 A1 | 2/2006 | Young et al. .............. 424/133.1 |
| 2006/0073572 A1* | 4/2006 | Huang et al. ................ 435/69.5 |
| 2006/0270003 A1 | 11/2006 | Arnott et al. ............. 435/69.52 |
| 2007/0160576 A1 | 7/2007 | Arnott et al. ................ 424/85.2 |

FOREIGN PATENT DOCUMENTS

EP       0 173 494      3/1986

(Continued)

OTHER PUBLICATIONS

Kawaguchi et al. 2004. J. Allergy Clin Immunol 114:1265-73.*

(Continued)

*Primary Examiner*—Gary B Nickol
*Assistant Examiner*—Shulamith H Shafer
(74) *Attorney, Agent, or Firm*—Fitzpatrick, Cella, Harper & Scinto

(57) ABSTRACT

The invention is related to findings that IL-17F-mediated inflammation of airway passages may be mediated via signaling through IL-17R on the basolateral surface of human respiratory epithelial cells. Thus, the present invention provides isolated and purified IL-17F or IL-17R polynucleotides and polypeptides. The present invention also is directed to novel methods for screening test compounds capable of inhibiting, i.e., decreasing, limiting, blocking, or otherwise reducing, IL-17F bioactivity, and methods for diagnosing, prognosing, and monitoring the progress of, disorders related to IL-17F bioactivity, e.g., disorders related to the effects of IL-17F binding to IL-17R on airway inflammation, e.g., in patients with cystic fibrosis, including pulmonary exacerbations due to bacterial infections in same. The present invention is further directed to novel therapeutics and therapeutic targets and to methods for the intervention (treatment) and prevention of said disorders related to IL-17F bioactivity.

8 Claims, 9 Drawing Sheets

FOREIGN PATENT DOCUMENTS

| | | |
|---|---|---|
| EP | 0 184 187 | 6/1986 |
| EP | 0 388 151 A1 | 9/1990 |
| EP | 0 125 023 | 6/1991 |
| EP | 0 171 496 | 5/1993 |
| EP | 0 433 225 B1 | 4/1999 |
| GB | 2 188 638 A | 10/1987 |
| WO | WO 86/01533 | 3/1986 |
| WO | WO 87/02671 | 5/1987 |
| WO | WO 91/00906 | 1/1991 |
| WO | WO 91/10741 | 7/1991 |
| WO | WO 92/03917 | 3/1992 |
| WO | WO 92/03918 | 3/1992 |
| WO | WO 94/02602 | 2/1994 |
| WO | WO 95/18826 | 1/1995 |
| WO | WO 96/33735 | 10/1996 |
| WO | WO 96/34096 | 10/1996 |
| WO | WO 99/51259 | 10/1999 |
| WO | WO 00/56772 | 9/2000 |
| WO | WO 02/064739 | 8/2002 |
| WO | WO 2005/010044 | 2/2005 |
| WO | WO 2005/123778 | 12/2005 |

OTHER PUBLICATIONS

Vilcek teaches 2003."The Cytokine Handbook" Chapter 1, p. 6.*
Chen et al. 2003. J Biol Chem. 278:17036-17043.*
Ratjen et al. 2003. Lancet 361:681-689.*
Aggarwal and Gurney (2002) "IL-17: prototype member of an emerging cytokine family" *J. Leukoc. Biol.* 71:1-8.
Aggarwal et al. (2003) "Interleukin-23 Promotes a Distinct CD4 T Cell Activation State Characterized by the Production of Interleukin-17" *J. Biol. Chem.* 278(3):1910-14.
Alfarano et al. (2005) "The Biomolecular Interaction Network Database and related tools 2005 update" *Nucleic Acids Res.* 33 Database Issue: D418-24.
Arts et al. (2003) "Adenoviral Vectors Expressing siRNAs for Discovery and Validation of Gene Function" *Genome Res.* 13:2325-32.
Bass (2001) "RNA interference: The short answer" *Nature* 411:428-29.
Bettelli and Kuchroo (2005) "IL-12- and IL-23-induced T helper cell subsets: birds of the same feather flock together" *J. Exp. Med.* 201:169-71.
Bockamp et al. (2002) "Of mice and models: improved animal models for biomedical research" *Physiol. Genomics* 11:115-32.
Chmiel et al. (2002) "The Role of Inflammation in the Pathophysiology of CF Lung Disease" *Clin. Rev. Allergy Immunol.* 23:5-27.
Davis et al. (2005) "Crystal structure of prostate-specific membrane antigen, a tumor marker and peptidase" *Proc. Natl. Acad. Sci. USA* 102:5981-86.
Devor et al. (2000) "Pharmacological modulation of ion transport across wild-type and ΔF508 CFTR-expressing human bronchial epithelia" *Am. J. Physiol. Cell Physiol.* 279:C461-79.
Dorn et al. (2004) "siRNA relieves chronic neuropathic pain" *Nucleic Acids Res.* 32(5):e49.
Eijnden et al. (2005) "IL-23 up-regulates IL-10 and induces IL-17 synthesis by polyclonally activated naive T cells in human" *Eur. J. Immunol.* 35:469-75.
Elbashir et al. (2001) "Duplexes of 21-nucleotide RNAs mediate RNA interference in cultured mammalian cells" *Nature* 411:494-98.
Elbashir et al. (2001) "Functional anatomy of siRNAs for mediating efficient RNAi in *Drosophila melanogaster* embryo lysate" *EMBO J.* 20:6877-88.
Elit (2002) "CCI-779 Wyeth" *Curr. Opin. Investig. Drugs* 3(8):1249-53.
Ferretti et al. (2003) "IL-17, Produced by Lymphocytes and Neutrophils, Is Necessary for Lipopolysaccharide-Induced Airway Neutrophilia: IL-15 as a Possible Trigger" *J. Immunol.* 170:2106-12.
Fujino et al. (2003) "Increased Expression of interleukin 17 in inflammatory bowel disease" *Gut* 52:65-70.
Galderisi et al. (1999) "Antisense Oligonucleotides as Therapeutic Agents" *J. Cell Physiol.* 181:251-57.

Halpin and Harbury (2004) "DNA Display II. Genetic Manipulation of Combinatorial Chemistry Libraries for Small-Molecule Evolution" *PLoS Biology* 2:1022-30.
Happel et al. (2003) "Cutting Edge: Roles of Toll-Like Receptor 4 and IL-23 in IL-17 Expression in Response to *Klebsiella pneumoniae* Infection" *J. Immunol.* 170:4432-36.
Heasman (2002) "Morpholino Oligos: Making Sense of Antisense?" *Dev. Biol.* 243:209-14.
Hellings et al. (2003) "Interleukin-17 Orchestrates the Granulocyte Influx into Airways after Allergen Inhalation in a Mouse Model of Allergic Asthma" *Am. J. Respir. Cell Mol. Biol.* 28:42-50.
Huang et al. (2002) "Inhibitors of mammalian target of rapamycin as novel antitumor agents: From bench to clinic" *Curr. Opin. Investig. Drugs* 3(2):295-304.
Hurst et al. (2002) "New IL-17 Family Members Promote Th1 or Th2 Responses in the Lung: In Vivo Function of the Novel Cytokine IL-25" *J. Immunol.* 169:443-53.
Hymowitz et al. (2001) "IL-17s adopt a cystine knot fold: structure and activity of a novel cytokine, IL-17F, and implications for receptor binding" *EMBO J.* 20:5332-41.
Jones and Chan (2002) "Interleukin-17 Stimulates the Expression of Interleukin-8, Growth-Related Oncogene-α, and Granulocyte-Colony-Stimulating Factor by Human Airway Epithelial Cells" *Am. J. Respir. Cell Mol. Biol.* 26:748-53.
Karp (2000) "An ontology for biological function based on molecular interactions" *Bioinformatics Ontology* 16:269-85.
Kawaguchi et al. (2001) "Identification of a Novel Cytokine, ML-1, and Its Expression in Subjects with Asthma" *J. Immunol.* 167:4430-35.
Knauert and Glazer (2001) "Triplex forming oligonucleotides: sequence-specific tools for gene targeting" *Hum. Mol. Genet.* 10:2243-51.
Kolls and Linden (2004) "Interleukin-17 Family Members and Inflammation" *Immunity* 21:467-76.
Kolls et al. (2003) "Interleukin-17: An Emerging Role in Lung Inflammation" *Am. J. Respir. Cell Mol. Biol.* 28:9-11.
Kuestner et al. (2004) "Identification of the IL-17 Receptor-related molecule, IL-17RC as a receptor for IL-17A and IL-17F" abstract for 18th International Mouse Genome Conference, Oct. 17-22, Seattle, USA.
Kuestner et al. (2005) "Human and mouse IL-17A and IL-17F differentially bind IL-17RA and IL-17RC" *Keystone Symposia: Cytokines, Disease and Therapeutic Intervention*, Keystone Symposia Publishing, Silverthorne, CO, Abstract No. 206, p. 49.
Kuwana (2002) "Induction of Anergic and Regulatory T Cells by Plasmacytoid Dendritic Cells and Other Dendritic Cell Subsets" *Hum. Immunol.* 63:1156-63.
Laan et al. (1999) "Neutrophil Recruitment by Human IL-17 Via C-X-C Chemokine Release in the Airways" *J. Imrnunol.* 162:2347-52.
Langrish et al. (2005) "IL-23 drives a pathogenic T cell population that induces autoimmune inflammation" *J. Exp. Med.* 201:233-40.
Lee et al. (2001) "IL-17E, a Novel Proinflammatory Ligand for the IL-17 Receptor Homolog IL-17RH1" *J. Biol. Chem.* 276:1660-64.
Li et al. (2000) "Cloning and characterization of IL-17B and IL-17C, two new members of the IL-17 cytokine family" *Proc. Natl. Acad. Sci. USA* 97:773-78.
Lindén et al. (2000) "Airway neutrophils and interleukin-17" *Eur. Respir. J.* 15:973-77.
Lindén and Adachi (2002) "Neutrophilic airway inflammation and IL-17" *Allergy* 57:769-75.
Patel (1997) "Structural analysis of nucleic acid aptamers" *Curr. Opin. Chem. Biol.* 1:32-46.
Rifle et al. (2002) "Dendritic Cells and Second Signal Blockade: a Step Toward Allograft Tolerance?" *Transplantation* 73:S1-S2.
Reynolds et al. (2004) "Rational siRNA design for RNA interference" *Nature Biotechnol.* 22:326-30.
Sagel et al. (2001) "Airway Inflammation in Children with Cystic Fibrosis and Healthy Children Assessed by Sputum Induction" *Am. J. Respir. Crit. Care Med.* 164:1425-31.
Schwarzenberger et al. (1998) "IL-17 Stimulates Granulopoiesis in Mice: Use of an Alternate, Novel Gene Therapy-Derived Method for In Vivo Evaluation of Cytokines" *J. Immunol.* 161:6383-89.

Schwarzenberger et al. (2000) "Requirement of Endogenous Stem Cell Favor and Granulocyte-Colony-Stimulating Factor for IL-17-Mediated Granulopoiesis" *J. Immunol.* 164:4783-89.

Shen et al. (2005) "Cytokines link osteoblasts and inflammation: microarray analysis of interleukin-17 and TNF-α-induced genes in bone cells" *J. Leukoc. Biol.* 77:388-99.

Shi et al. (2000) "A Novel Cytokine Receptor-Ligand Pair: Identification, Molecular Characterization, And In Vivo Immunomodulatory Activity" *J. Biol. Chem.* 275:19167-76.

Sioud (2001) "Nucleic Acid Enzymes as a Novel Generation of Anti-gene Agents" *Curr. Mol. Med.* 1:575-88.

Smountas et al. (2004) "Induced sputum in cystic fibrosis: within-week reproducibility of inflammatory markers" *Clin. Biochem* 37:1031-36.

Song et al. (2003) "RNA inteference targeting Fas protects mice from fulminant hepatitis" *Nature Med.* 9:347-51.

Starnes et al. (2001) "Cutting Edge: IL-17F, a Novel Cytokine Selectively Expressed in Activated T Cells and Monocytes, Regulates Angiogenesis and Endothelial Cell Cytokine Production" *J. Immunol.* 67:4137-40.

Starnes et al. (2002) "Cutting Edge: IL-17D, a Novel Member of the IL-17 Family, Stimulates Cytokine Production and Inhibits Hemopoiesis" *J. Immunol.* 169:642-46.

Sui et al. (2002) "A DNA vector-based RNAi technology to suppress gene expression in mammalian cells" *Proc. Natl. Acad. Sci. USA* 99:5515-20.

Verkman (2004) "Drug discovery in academia" *Am. J. Physiol. Cell Physiol.* 286:465-74.

Wolfer et al. (2002) "Knockout mice: simple solutions to the problems of genetic background and flanking genes" *Trends Neurosci.* 25:336-40.

Xiao et al. (2003) "Dendritic Cell Vaccine Design: Strategies for Eliciting Peripheral Tolerance as Therapy of Autoimmune Diseases" *Biodrugs* 17:103-11.

Yagi et al. (2005) "Intrajoint comparisons of gene expression patterns in human osteoarthritis suggest a change in chondrocyte phenotype" *J. Orthop. Res.* 23:1128-38.

Yao et al. (1996) "Complete nucleotide sequence of the mouse CTLA8 gene" *Gene* 168:223-25.

Yao et al. (1995) "Human IL-17: A Novel Cytokine Derived from T Cells" *J. Immunol.* 155:5483-86.

Ye et al. (2001) "Interleukin-17 and Lung Host Defense against *Klebsiella pneumoniae* Infection" *Am. J. Respir. Cell Mol. Biol.* 25:335-40.

Ye et al. (2001) "Requirement of Interleukin-17 Receptor Signaling for Lung CXC Chemokine and Granulocyte Colony-stimulating Factor Expression, Neutrophil Recruitment, and Host Defense" *J. Exp. Med.* 194:519-27.

Yu et al. (2002) "RNA interference by expression of short-interfering RNAs and hairpin RNAs in mammalian cells" *Proc. Natl. Acad. Sci. USA* 99:6047-52.

Yusuf-Makagiansar et al. (2002) "Inhibition of LFA-1/ICAM-1 and VLA-4/VCAM-1 as a Therapeutic Approach to Inflammation and Autoimmune Disease" *Med. Res. Rev.* 22:146-67.

NCBI Accession No. Q61453, printed Jun. 6, 2008, 3 pages.

Lock et al. (2002) "Gene-microarray analysis of multiple sclerosis lesions yields new targets validated in autoimmune encephalomyelitis" *Nat. Med.* 8:500-08.

Lu and Thomson (2002) "Manipulation of Dendritic Cells for Tolerance Induction in Transplantation and Autoimmune Disease" *Transplantation* 73:S19-S22.

Lubberts (2003) "The role of IL-17 and family members in the pathogenesis of arthritis" *Curr. Opin. Investig. Drugs* 4:572-77.

Mallat et al. (2001) "Interleukin-18/Interleukin-18 Binding Protein Signaling Modulates Atherosclerotic Lesion Development and Stability" *Circ. Res.* 89:e41-45.

Mancini et al. (2004) "The Management of Immunosuppression: The Art and the Science" *Crit. Care. Nurs. Q.* 27:61-64.

McAllister et al. (2005) "Role of IL-17A, IL-17F, and the IL-17 Receptor in Regulating Growth-Related Oncogene-α and Granulocyte Colony-Stimulating Factor in Bronchial Epithelium: Implications for Airway Inflammation in Cystic Fibrosis" *J. Immunol.* 175:404-12.

Micklefield (2001) "Backbone Modification of Nucleic Acids: Synthesis, Structure and Therapeutic Applications" *Curr. Med. Chem.* 8:1157-79.

Moseley et al. (2003) "Interleukin-17 family and IL-17 Receptors" *Cytokine Growth Factor Rev.* 14: 155-74.

Nakae et al. (2003) "Suppression of Immune Induction of Collagen-Induced Arthritis in IL-17 Deficient Mice" *J. Immunol.* 171:6173-77.

Neidhart et al. (2000) "Anti-Interleukin-1 and Anti-CD44 Interventions Producing Significant Inhibition of Cartilage Destruction in an In Vitro Model of Cartilage Invasion by Rheumatoid Arthritis Synovial Fibroblast" *Arth. Rheum.* 43:1719-28.

Numasaki et al. (2004) "Regulatory roles of IL-17 and IL-17F in G-CSF production by lung microvascular endothelial cells stimulated with IL-1β and/or TNF-α" *Immunol. Lett.* 95:97-104.

Nimjee et al. (2005) "Aptamers: An Emerging Class of Therapeutics" *Annu. Rev. Med.* 56:555-83.

Oda et al. (2005) "Interleukin-17F Induces Pulmonary Neutrophilia and Amplifies Antigen-Induced Allergic Response," *Am. J. Respir. Crit. Care Med.* 171:12-18.

Paddison et al. (2002) "Stable suppression of gene expression by RNAi in mammalian cells" *Proc. Natl. Acad. Sci. USA* 99:1443-48.

R&D Systems Product Sheet for Catalog No. 317-ILB, Recombinant Human IL-17, revised Aug. 12, 2009, 1 page.

R&D Systems IL-17 Catalog Products, printed Aug. 27, 2009, 1 page.

Swiss-Prot Accession No. 16552 (1996), printed Sep. 2, 2009, 6 pages.

\* cited by examiner

SEQUENCE LISTING

```
<160> NUMBER OF SEQ ID NOS: 5

<210> SEQ ID NO 1
<211> LENGTH: 492
<212> TYPE: DNA
<213> ORGANISM: Homo sapiens
<220> FEATURE:
<221> NAME/KEY: CDS
<222> LOCATION: (1)..(492)

<400> SEQUENCE: 1 atg aca gtg aag acc ctg cat ggc cca gcc atg gtc aag tac ttg ctg      48
Met Thr Val Lys Thr Leu His Gly Pro Ala Met Val Lys Tyr Leu Leu
1               5                   10                  15 ctg tcg ata ttg ggg ctt gcc ttt ctg agt gag gcg gca gct cgg aaa      96
Leu Ser Ile Leu Gly Leu Ala Phe Leu Ser Glu Ala Ala Ala Arg Lys
            20                  25                  30 atc ccc aaa gta gga cat act ttt ttc caa aag cct gag agt tgc ccg     144
Ile Pro Lys Val Gly His Thr Phe Phe Gln Lys Pro Glu Ser Cys Pro
        35                  40                  45 cct gtc cca gga ggt agt atg aag ctt gac att ggc atc atc aat gaa     192
Pro Val Pro Gly Gly Ser Met Lys Leu Asp Ile Gly Ile Ile Asn Glu
    50                  55                  60 aac cag cgc gtt tcc atg tca cgt aac atc gag agc cgc tcc acc tcc     240
Asn Gln Arg Val Ser Met Ser Arg Asn Ile Glu Ser Arg Ser Thr Ser
65                  70                  75                  80 ccc tgg aat tac act gtc act tgg gac ccc aac cgg tac ccc tcg gaa     288
Pro Trp Asn Tyr Thr Val Thr Trp Asp Pro Asn Arg Tyr Pro Ser Glu
                85                  90                  95 gtt gta cag gcc cag tgt agg aac ttg ggc tgc atc aat gct caa gga     336
Val Val Gln Ala Gln Cys Arg Asn Leu Gly Cys Ile Asn Ala Gln Gly
            100                 105                 110 aag gaa gac atc tcc atg aat tcc gtt ccc atc cag caa gag acc ctg     384
Lys Glu Asp Ile Ser Met Asn Ser Val Pro Ile Gln Gln Glu Thr Leu
        115                 120                 125 gtc gtc cgg agg aag cac caa ggc tgc tct gtt tct ttc cag ttg gag     432
Val Val Arg Arg Lys His Gln Gly Cys Ser Val Ser Phe Gln Leu Glu
    130                 135                 140 aag gtg ctg gtg act gtt ggc tgc acc tgc gtc acc cct gtc atc cac     480
Lys Val Leu Val Thr Val Gly Cys Thr Cys Val Thr Pro Val Ile His
145                 150                 155                 160 cat gtg cag taa                                                      492
His Val Gln
```

<210> SEQ ID NO 2
<211> LENGTH: 163
<212> TYPE: PRT
<213> ORGANISM: Homo sapiens

<400> SEQUENCE: 2

```
Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Arg Lys
            20                  25                  30

Ile Pro Lys Val Gly His Thr Phe Phe Gln Lys Pro Glu Ser Cys Pro
        35                  40                  45

Pro Val Pro Gly Gly Ser Met Lys Leu Asp Ile Gly Ile Asn Glu
    50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160

His Val Gln
```

<210> SEQ ID NO 3
<211> LENGTH: 3420
<212> TYPE: DNA
<213> ORGANISM: Homo sapiens
<220> FEATURE:
<221> NAME/KEY: CDS
<222> LOCATION: (134)..(2734)

<400> SEQUENCE: 3

```
ggctggaagc cggaagcgag caaagtggag ccgactcgaa ctccaccggc acgagggcgg      60
aaaagaaagc ctcagaacgt tcgctcgctg cgtccccagc cggggccgag ccctccgcga     120
cgccacccgg gcc atg ggg gcc gca cgc agc ccg ccg tcc gct gtc ccg        169
            Met Gly Ala Ala Arg Ser Pro Pro Ser Ala Val Pro
            1               5                   10 ggg ccc ctg ctg ggg ctg ctc ctg ctg ctc ctg ggc gtg ctg gcc cgg       217
Gly Pro Leu Leu Gly Leu Leu Leu Leu Leu Leu Gly Val Leu Ala Pro
                15                  20                  25 ggt ggc gcc tcc ctg cga ctc ctg gac cac cgg gcg ctg gtc tgc tcc       265
Gly Gly Ala Ser Leu Arg Leu Leu Asp His Arg Ala Leu Val Cys Ser
        30                  35                  40 cag ccg ggg cta aac tgc acg gtc aag aat agt acc tgc ctg gat gac       313
Gln Pro Gly Leu Asn Cys Thr Val Lys Asn Ser Thr Cys Leu Asp Asp
45                  50                  55                  60 agc tgg att cac cct cga aac ctg acc ccc tcc tcc cca aag gac ctg       361
Ser Trp Ile His Pro Arg Asn Leu Thr Pro Ser Ser Pro Lys Asp Leu
                65                  70                  75 cag atc cag ctg cac ttt gcc cac acc caa caa gga gac ctg ttc ccc       409
Gln Ile Gln Leu His Phe Ala His Thr Gln Gln Gly Asp Leu Phe Pro
            80                  85                  90 gtg gct cac atc gaa tgg aca ctg cag aca gac gcc agc atc ctg tac       457
```

```
                Val Ala His Ile Glu Trp Thr Leu Gln Thr Asp Ala Ser Ile Leu Tyr
                     95                 100                 105 ctc gag ggt gca gag tta tct gtc ctg cag ctg aac acc aat gaa cgt        505
Leu Glu Gly Ala Glu Leu Ser Val Leu Gln Leu Asn Thr Asn Glu Arg
    110                 115                 120 ttg tgc gtc agg ttt gag ttt ctg tcc aaa ctg agg cat cac cac agg        553
Leu Cys Val Arg Phe Glu Phe Leu Ser Lys Leu Arg His His His Arg
125                 130                 135                 140 cgg tgg cgt ttt acc ttc agc cac ttt gtg gtt gac cct gac cag gaa        601
Arg Trp Arg Phe Thr Phe Ser His Phe Val Val Asp Pro Asp Gln Glu
                145                 150                 155 tat gag gtg acc gtt cac cac ctg ccc aag ccc atc cct gat ggg gac        649
Tyr Glu Val Thr Val His His Leu Pro Lys Pro Ile Pro Asp Gly Asp
        160                 165                 170 cca aac cac cag tcc aag aat ttc ctt gtg cct gac tgt gag cac gcc        697
Pro Asn His Gln Ser Lys Asn Phe Leu Val Pro Asp Cys Glu His Ala
            175                 180                 185 agg atg aag gta acc acg cca tgc atg agc tca ggc agc ctg tgg gac        745
Arg Met Lys Val Thr Thr Pro Cys Met Ser Ser Gly Ser Leu Trp Asp
                190                 195                 200 ccc aac atc acc gtg gag acc ctg gag gcc cac cag ctg cgt gtg agc        793
Pro Asn Ile Thr Val Glu Thr Leu Glu Ala His Gln Leu Arg Val Ser
205                 210                 215                 220 ttc acc ctg tgg aac gaa tct acc cat tac cag atc ctg ctg acc agt        841
Phe Thr Leu Trp Asn Glu Ser Thr His Tyr Gln Ile Leu Leu Thr Ser
                225                 230                 235 ttt ccg cac atg gag aac cac agt tgc ttt gag cac atg cac cac ata        889
Phe Pro His Met Glu Asn His Ser Cys Phe Glu His Met His His Ile
            240                 245                 250 cct gcg ccc aga cca gaa gag ttc cac cag cga tcc aac gtc aca ctc        937
Pro Ala Pro Arg Pro Glu Glu Phe His Gln Arg Ser Asn Val Thr Leu
                255                 260                 265 act cta cgc aac ctt aaa ggg tgc tgt cgc cac caa gtg cag atc cag        985
Thr Leu Arg Asn Leu Lys Gly Cys Cys Arg His Gln Val Gln Ile Gln
270                 275                 280 ccc ttc ttc agc agc tgc ctc aat gac tgc ctc aga cac tcc gcg act       1033
Pro Phe Phe Ser Ser Cys Leu Asn Asp Cys Leu Arg His Ser Ala Thr
285                 290                 295                 300 gtt tcc tgc cca gaa atg cca gac act cca gaa cca att ccg gac tac       1081
Val Ser Cys Pro Glu Met Pro Asp Thr Pro Glu Pro Ile Pro Asp Tyr
                305                 310                 315 atg ccc ctg tgg gtg tac tgg ttc atc acg ggc atc tcc atc ctg ctg       1129
Met Pro Leu Trp Val Tyr Trp Phe Ile Thr Gly Ile Ser Ile Leu Leu
            320                 325                 330 gtg ggc tcc gtc atc ctg ctc atc gtc tgc atg acc tgg agg cta gct       1177
Val Gly Ser Val Ile Leu Leu Ile Val Cys Met Thr Trp Arg Leu Ala
                335                 340                 345 ggg cct gga agt gaa aaa tac agt gat gac acc aaa tac acc gat ggc       1225
Gly Pro Gly Ser Glu Lys Tyr Ser Asp Asp Thr Lys Tyr Thr Asp Gly
350                 355                 360 ctg cct gcg gct gac ctg atc ccc cca ccg ctg aag ccc agg aag gtc       1273
Leu Pro Ala Ala Asp Leu Ile Pro Pro Pro Leu Lys Pro Arg Lys Val
365                 370                 375                 380 tgg atc atc tac tca gcc gac cac ccc ctc tac gtg gac gtg gtc ctg       1321
Trp Ile Ile Tyr Ser Ala Asp His Pro Leu Tyr Val Asp Val Val Leu
                385                 390                 395 aaa ttc gcc cag ttc ctg ctc acc gcc tgc ggc acg gaa gtg gcc ctg       1369
Lys Phe Ala Gln Phe Leu Leu Thr Ala Cys Gly Thr Glu Val Ala Leu
                400                 405                 410
```

```
                                                              -continued gac ctg ctg gaa gag cag gcc atc tcg gag gca gga gtc atg acc tgg      1417
Asp Leu Leu Glu Glu Gln Ala Ile Ser Glu Ala Gly Val Met Thr Trp
            415                 420                 425 gtg ggc cgt cag aag cag gag atg gtg gag agc aac tct aag atc atc      1465
Val Gly Arg Gln Lys Gln Glu Met Val Glu Ser Asn Ser Lys Ile Ile
        430                 435                 440 gtc ctg tgc tcc cgc ggc acg cgc gcc aag tgg cag gcg ctc ctg ggc      1513
Val Leu Cys Ser Arg Gly Thr Arg Ala Lys Trp Gln Ala Leu Leu Gly
445                 450                 455                 460 cgg ggg gcg cct gtg cgg ctg cgc tgc gac cac gga aag ccc gtg ggg      1561
Arg Gly Ala Pro Val Arg Leu Arg Cys Asp His Gly Lys Pro Val Gly
                465                 470                 475 gac ctg ttc act gca gcc atg aac atg atc ctc ccg gac ttc aag agg      1609
Asp Leu Phe Thr Ala Ala Met Asn Met Ile Leu Pro Asp Phe Lys Arg
            480                 485                 490 cca gcc tgc ttc ggc acc tac gta gtc tgc tac ttc agc gag gtc agc      1657
Pro Ala Cys Phe Gly Thr Tyr Val Val Cys Tyr Phe Ser Glu Val Ser
        495                 500                 505 tgt gac ggc gac gtc ccc gac ctg ttc ggc gcg gcc ccg cgg tac ccg      1705
Cys Asp Gly Asp Val Pro Asp Leu Phe Gly Ala Ala Pro Arg Tyr Pro
510                 515                 520 ctc atg gac agg ttc gag gag gtg tac ttc cgc atc cag gac ctg gag      1753
Leu Met Asp Arg Phe Glu Glu Val Tyr Phe Arg Ile Gln Asp Leu Glu
525                 530                 535                 540 atg ttc cag ccg ggc cgc atg cac cgc gta ggg gag ctg tcg ggg gac      1801
Met Phe Gln Pro Gly Arg Met His Arg Val Gly Glu Leu Ser Gly Asp
            545                 550                 555 aac tac ctg cgg agc ccg ggc ggc agg cag ctc cgc gcc gcc ctg gac      1849
Asn Tyr Leu Arg Ser Pro Gly Gly Arg Gln Leu Arg Ala Ala Leu Asp
        560                 565                 570 agg ttc cgg gac tgg cag gtc cgc tgt ccc gac tgg ttc gaa tgt gag      1897
Arg Phe Arg Asp Trp Gln Val Arg Cys Pro Asp Trp Phe Glu Cys Glu
575                 580                 585 aac ctc tac tca gca gat gac cag gat gcc ccg tcc ctg gac gaa gag      1945
Asn Leu Tyr Ser Ala Asp Asp Gln Asp Ala Pro Ser Leu Asp Glu Glu
            590                 595                 600 gtg ttt gag gag cca ctg ctg cct ccg gga acc ggc atc gtg aag cgg      1993
Val Phe Glu Glu Pro Leu Leu Pro Pro Gly Thr Gly Ile Val Lys Arg
605                 610                 615                 620 gcg ccc ctg gtg cgc gag cct ggc tcc cag gcc tgc ctg gcc ata gac      2041
Ala Pro Leu Val Arg Glu Pro Gly Ser Gln Ala Cys Leu Ala Ile Asp
                625                 630                 635 ccg ctg gtc ggg gag gaa gga gga gca gca gtg gca aag ctg gaa cct      2089
Pro Leu Val Gly Glu Glu Gly Gly Ala Ala Val Ala Lys Leu Glu Pro
            640                 645                 650 cac ctg cag ccc cgg ggt cag cca gcg ccg cag ccc ctc cac acc ctg      2137
His Leu Gln Pro Arg Gly Gln Pro Ala Pro Gln Pro Leu His Thr Leu
        655                 660                 665 gtg ctc gcc gca gag gag ggg gcc ctg gtg gcc gcg gtg gag cct ggg      2185
Val Leu Ala Ala Glu Glu Gly Ala Leu Val Ala Ala Val Glu Pro Gly
    670                 675                 680 ccc ctg gct gac ggt gcc gca gtc cgg ctg gca ctg gcg ggg gag ggc      2233
Pro Leu Ala Asp Gly Ala Ala Val Arg Leu Ala Leu Ala Gly Glu Gly
685                 690                 695                 700 gag gcc tgc ccg ctg ctg ggc agc ccg ggc gct ggg cga aat agc gtc      2281
Glu Ala Cys Pro Leu Leu Gly Ser Pro Gly Ala Gly Arg Asn Ser Val
                705                 710                 715 ctc ttc ctc ccc gtg gac ccc gag gac tcg ccc ctt ggc agc agc acc      2329
Leu Phe Leu Pro Val Asp Pro Glu Asp Ser Pro Leu Gly Ser Ser Thr
            720                 725                 730
```

-continued

```
ccc atg gcg tct cct gac ctc ctt cca gag gac gtg agg gag cac ctc      2377
Pro Met Ala Ser Pro Asp Leu Leu Pro Glu Asp Val Arg Glu His Leu
        735                 740                 745 gaa ggc ttg atg ctc tcg ctc ttc gag cag agt ctg agc tgc cag gcc      2425
Glu Gly Leu Met Leu Ser Leu Phe Glu Gln Ser Leu Ser Cys Gln Ala
    750                 755                 760 cag ggg ggc tgc agt aga ccc gcc atg gtc ctc aca gac cca cac acg      2473
Gln Gly Gly Cys Ser Arg Pro Ala Met Val Leu Thr Asp Pro His Thr
765                 770                 775                 780 ccc tac gag gag gag cag cgg cag tca gtg cag tct gac cag ggc tac      2521
Pro Tyr Glu Glu Glu Gln Arg Gln Ser Val Gln Ser Asp Gln Gly Tyr
                785                 790                 795 atc tcc agg agc tcc ccg cag ccc ccc gag gga ctc acg gaa atg gag      2569
Ile Ser Arg Ser Ser Pro Gln Pro Pro Glu Gly Leu Thr Glu Met Glu
            800                 805                 810 gaa gag gag gaa gag gag cag gac cca ggg aag ccg gcc ctg cca ctc      2617
Glu Glu Glu Glu Glu Glu Gln Asp Pro Gly Lys Pro Ala Leu Pro Leu
        815                 820                 825 tct ccc gag gac ctg gag agc ctg agg agc ctc cag cgg cag ctg ctt      2665
Ser Pro Glu Asp Leu Glu Ser Leu Arg Ser Leu Gln Arg Gln Leu Leu
    830                 835                 840 ttc cgc cag ctg cag aag aac tcg ggc tgg gac acg atg ggg tca gag      2713
Phe Arg Gln Leu Gln Lys Asn Ser Gly Trp Asp Thr Met Gly Ser Glu
845                 850                 855                 860 tca gag ggg ccc agt gca tga gggcggctcc ccagggaccg cccagatccc        2764
Ser Glu Gly Pro Ser Ala
                865 agctttgaga gaggagtgtg tgtgcacgta ttcatctgtg tgtacatgtc tgcatgtgta    2824 tatgttcgtg tgtgaaatgt aggctttaaa atgtaaatgt ctggatttta atcccaggca    2884 tccctcctaa cttttctttg tgcagcggtc tggttatcgt ctatcccag gggaatccac     2944 acagcccgct cccaggagct aatggtagag cgtccttgag gctccattat tcgttcattc    3004 agcatttatt gtgcacctac tatgtggcgg gcatttggga taccaagata aattgcatgc    3064 ggcatggccc cagccatgaa ggaacttaac cgctagtgcc gaggacacgt taaacgaaca    3124 ggatgggccg ggcacggtgg ctcacgcctg taatcccagc acactgggag gccgaggcag    3184 gtggatcact ctgaggtcag gagtttgagc agcctggcc aacatggtga acccccatct     3244 ccactaaaaa tagaaaaatt agccgggcat ggtgacacat gcctgtagtc ctagctactt    3304 gggaggctga ggcaggagaa ttgcttgaat ctgggaggca gaggttgcag tgagccgaga    3364 ttgtgccatt gcactgcagc ctggatgaca gagcgagact ctatctcaaa aaaaaa        3420
```

<210> SEQ ID NO 4
<211> LENGTH: 866
<212> TYPE: PRT
<213> ORGANISM: Homo sapiens

<400> SEQUENCE: 4

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60
```

```
Pro Arg Asn Leu Thr Pro Ser Ser Pro Lys Asp Leu Gln Ile Gln Leu
 65              70                  75                  80

His Phe Ala His Thr Gln Gln Gly Asp Leu Phe Pro Val Ala His Ile
             85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
130                 135                 140

Thr Phe Ser His Phe Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
                180                 185                 190

Thr Thr Pro Cys Met Ser Ser Gly Ser Leu Trp Asp Pro Asn Ile Thr
                195                 200                 205

Val Glu Thr Leu Glu Ala His Gln Leu Arg Val Ser Phe Thr Leu Trp
            210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
                275                 280                 285

Ser Cys Leu Asn Asp Cys Leu Arg His Ser Ala Thr Val Ser Cys Pro
            290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
                340                 345                 350

Glu Lys Tyr Ser Asp Asp Thr Lys Tyr Thr Asp Gly Leu Pro Ala Ala
                355                 360                 365

Asp Leu Ile Pro Pro Pro Leu Lys Pro Arg Lys Val Trp Ile Ile Tyr
            370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
                435                 440                 445

Arg Gly Thr Arg Ala Lys Trp Gln Ala Leu Leu Gly Arg Gly Ala Pro
            450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
```

-continued

```
                485                 490                 495
Gly Thr Tyr Val Val Cys Tyr Phe Ser Glu Val Ser Cys Asp Gly Asp
                500                 505                 510
Val Pro Asp Leu Phe Gly Ala Ala Pro Arg Tyr Pro Leu Met Asp Arg
                515                 520                 525
Phe Glu Glu Val Tyr Phe Arg Ile Gln Asp Leu Glu Met Phe Gln Pro
                530                 535                 540
Gly Arg Met His Arg Val Gly Glu Leu Ser Gly Asp Asn Tyr Leu Arg
545                 550                 555                 560
Ser Pro Gly Gly Arg Gln Leu Arg Ala Ala Leu Asp Arg Phe Arg Asp
                565                 570                 575
Trp Gln Val Arg Cys Pro Asp Trp Phe Glu Cys Glu Asn Leu Tyr Ser
                580                 585                 590
Ala Asp Asp Gln Asp Ala Pro Ser Leu Asp Glu Glu Val Phe Glu Glu
                595                 600                 605
Pro Leu Leu Pro Pro Gly Thr Gly Ile Val Lys Arg Ala Pro Leu Val
                610                 615                 620
Arg Glu Pro Gly Ser Gln Ala Cys Leu Ala Ile Asp Pro Leu Val Gly
625                 630                 635                 640
Glu Glu Gly Gly Ala Ala Val Ala Lys Leu Glu Pro His Leu Gln Pro
                645                 650                 655
Arg Gly Gln Pro Ala Pro Gln Pro Leu His Thr Leu Val Leu Ala Ala
                660                 665                 670
Glu Glu Gly Ala Leu Val Ala Ala Val Glu Pro Gly Pro Leu Ala Asp
                675                 680                 685
Gly Ala Ala Val Arg Leu Ala Leu Ala Gly Glu Gly Glu Ala Cys Pro
                690                 695                 700
Leu Leu Gly Ser Pro Gly Ala Gly Arg Asn Ser Val Leu Phe Leu Pro
705                 710                 715                 720
Val Asp Pro Glu Asp Ser Pro Leu Gly Ser Ser Thr Pro Met Ala Ser
                725                 730                 735
Pro Asp Leu Leu Pro Glu Asp Val Arg Glu His Leu Glu Gly Leu Met
                740                 745                 750
Leu Ser Leu Phe Glu Gln Ser Leu Ser Cys Gln Ala Gln Gly Gly Cys
                755                 760                 765
Ser Arg Pro Ala Met Val Leu Thr Asp Pro His Thr Pro Tyr Glu Glu
770                 775                 780
Glu Gln Arg Gln Ser Val Gln Ser Asp Gln Gly Tyr Ile Ser Arg Ser
785                 790                 795                 800
Ser Pro Gln Pro Pro Glu Gly Leu Thr Glu Met Glu Glu Glu Glu Glu
                805                 810                 815
Glu Glu Gln Asp Pro Gly Lys Pro Ala Leu Pro Leu Ser Pro Glu Asp
                820                 825                 830
Leu Glu Ser Leu Arg Ser Leu Gln Arg Gln Leu Leu Phe Arg Gln Leu
                835                 840                 845
Gln Lys Asn Ser Gly Trp Asp Thr Met Gly Ser Glu Ser Glu Gly Pro
850                 855                 860
Ser Ala
865

<210> SEQ ID NO 5
<211> LENGTH: 21
<212> TYPE: PRT
<213> ORGANISM: Apis mellifera
```

```
<400> SEQUENCE: 5

Met Lys Phe Leu Val Asn Val Ala Leu Val Phe Met Val Val Tyr Ile
1               5                   10                  15

Ser Tyr Ile Tyr Ala
            20
```

USE OF IL-17F IN DIAGNOSIS AND THERAPY OF AIRWAY INFLAMMATION

RELATED APPLICATIONS

This application claims priority to U.S. Provisional Patent Application No. 60/653,186, filed Feb. 14, 2005, which is hereby incorporated by reference herein in its entirety.

BACKGROUND OF THE INVENTION

1. Field of the Invention

This invention relates to characterization of the effects of IL-17F binding to IL-17R; in particular, the invention relates to the effects of IL-17F binding to IL-17R on airway inflammation, e.g., in patients with cystic fibrosis, including pulmonary exacerbations due to bacterial infections in same.

2. Related Background Art

IL-17A is a proinflammatory cytokine that regulates both granulopoiesis and recruitment of neutrophils into sites of inflammation (Yao et al. (1995) *J. Immunol.* 155:5483-86; Ye et al. (2001) *J. Exp. Med.* 194:519-28; Kolls et al. (2003) *Am. J. Respir. Cell Mol. Biol.* 28:9-11; Laan et al. (1999) *J. Immunol.* 162:2347-52; Linden et al. (2000) *Eur. Respir. J.* 15:973-77). This is due, in part, to the ability of IL-17A to both induce the release of CXC chemokines and regulate the expression of G-CSF, a critical granulopoietic growth factor (Laan, supra; Moseley et al. (2003) *Cytokine Growth Factor Rev.* 14:155-74; Jones and Chan (2002) *Am. J. Respir. Cell Mol. Biol.* 26:748-53; Ye et al. (2001) *Am. J. Respir. Cell Mol. Biol.* 25:335-40; Ye et al. (2001) *J. Exp. Med.* 194:519-28). Mice with a homozygous deletion of the receptor to IL-17A, i.e., IL-17 receptor (IL-17R), have enhanced lethality, defective neutrophil recruitment, and decreased granulopoiesis to experimental Gram-negative pneumonia (Ye et al. (2001) *J. Exp. Med.* 194:519-28). However, they do not have an increased susceptibility to intracellular infections caused by *Listeria monocytogenes* or *Mycobacteria tuberculosis* (unpublished observations). This defect in host defense is likely due, in part, to a greater than 90% reduction in G-CSF in response to Gram-negative bacterial challenge in IL-17R-deficient mice compared to control mice, as well as a significantly attenuated response to infection (Ye et al. (2001) *J. Exp. Med.* 194:519-28).

Recently five other proteins, in addition to IL-17A, have been identified as members of the IL-17 family of proteins; IL-17F has the closest sequence homology (58% at the protein level) to IL-17A, as well as similar induction of CXC chemokines and similar neutrophil-mobilization profiles (Moseley et al., supra; Li et al. (2000) *Proc. Natl. Acad. Sci. USA* 97:773-78; Starnes et al. (2001) *J. Immunol.* 167:4137-40; Starnes et al. (2002) *J. Immunol.* 169:642-46; Hurst et al. (2002) *J. Immunol.* 169:443-53; Aggarwal and Gurney (2002) *J. Leukoc. Biol.* 71:1-8; Hymowitz et al. (2001) *EMBO J* 20:5332-41). IL-17A and IL-17F lie immediately adjacent to each other on mouse chromosome 1 and human chromosome 6, and both cytokines are produced by T cells in response to IL-23 (Chmiel et al. (2002) *Clin. Rev. Allergy Immunol.* 23:5-27; Aggarwal et al. (2003) *J. Biol. Chem.* 278(3):1910-14; Happel et al. (2003) *J. Immunol.* 170:4432-36; Kolls et al. (2004) *Immunity* 21:467-76). Furthermore, IL-17A and IL-17F are induced in a similar time course in the lung in experimental Gram-negative pneumonia (unpublished observations). Although IL-17F has a lower affinity for IL-17R, by an order of magnitude as compared to IL-17A, there has been some speculation as to whether both IL-17A and IL-17F signal via IL-17R because the two proteins share similar biological activities (Hymowitz et al., supra).

To date, the interaction between IL-17F and IL-17R has not been characterized. Consequently, a direct correlation between IL-17F-mediated signaling and airway inflammation has not been proven definitively. The present invention provides this correlation. In particular, the correlation provided by the present invention allows for the diagnosis, prognosis, monitoring and/or treating of airway inflammation, e.g., in patients with cystic fibrosis, including pulmonary exacerbations due to bacterial infections in same, via methods that detect IL-17F.

SUMMARY OF THE INVENTION

Methods of screening test compounds capable of inhibiting, e.g., decreasing, limiting, blocking, or otherwise reducing, IL-17F-mediated inflammation in the airways are disclosed. Also, methods of diagnosing, prognosing, monitoring and/or treating airway inflammation, e.g., in patients with cystic fibrosis, including pulmonary exacerbations due to bacterial infections in same, comprising detecting IL-17F are disclosed.

The inventors have shown that, in human lung, IL-17R is expressed in respiratory epithelial cells with a greater expression on basolateral surfaces compared to apical surfaces. Additionally, the increased expression of IL-17R on the basolateral surface of respiratory epithelial cells is correlated with a more potent induction of growth factors (e.g., IL-1β, IL-2, IL-4, IL-5, IL-6, IL-7, IL-8, IL-10, IL-12p70, IL-13, IL-17, G-CSF, GM-CSF, IFN-γ, MCP-1, MIP-1β, TNF-α, GRO-α, etc.) by basolaterally supplied IL-17F compared to apically supplied IL-17F. Among these induced growth factors, GRO-α, G-CSF, IL-6, and IL-8 demonstrated the greatest induction of expression in HBE cells from all donors tested (n>7). In addition, the inventors demonstrated that an inhibitory anti-IL-17R antibody significantly attenuated IL-17F-mediated induction of cytokine/chemokine production, providing further evidence that IL-17F induces cytokine/chemokine production in HBE cells by binding to IL-17R. The inventors also demonstrated that IL-17F was detectable in all tested samples collected on the first day of hospitalization from patients with cystic fibrosis who were also suffering from pulmonary exacerbation. Additionally, the inventors demonstrated that a significant decline in IL-17F levels in samples collected from these patients correlated with treatment of the pulmonary exacerbation.

Accordingly, in one aspect, the invention provides methods of screening test compounds capable of inhibiting, e.g., decreasing, limiting, blocking, or otherwise reducing, the interaction between IL-17F and IL-17R. The methods disclosed herein comprise the steps of contacting a sample containing IL-17F and IL-17R with the compound, and determining whether the interaction of IL-17F with IL-17R in the sample is decreased relative to the interaction of IL-17F with IL-17R in a sample not contacted with the compound, whereby a decrease in the interaction of IL-17F with IL-17R in the sample contacted with the compound identifies the compound as one that inhibits the interaction of IL-17F with IL-17R. In one embodiment of the invention, a decrease in the interaction of IL-17F with IL-17R is detected as a decrease in IL-17F-mediated induction of cytokine, chemokine, and/or growth factor expression.

In another aspect, the invention additionally features methods of diagnosing, prognosing, and/or monitoring a disorder related to IL-17F in a subject, comprising the steps of detecting a test amount of an IL-17F gene product in a sample from the subject, and comparing the test amount with a normal amount of the IL-17F gene product in a control sample, whereby a test amount significantly above the normal amount provides a positive indication in the diagnosis of a disorder related to IL-17F. In one embodiment of the invention, the methods are directed toward diagnosing, prognosing, and/or monitoring airway inflammation, e.g., airway inflammation that results in pulmonary exacerbation, airway inflammation caused by an infectious agent, airway inflammation in a patient with cystic fibrosis, etc. In other embodiments, the methods of the invention involve detecting an IL-17F protein, e.g., with an anti-IL-17F antibody.

In another aspect, the invention provides methods of treating a subject at risk for, or diagnosed with, airway inflammation, e.g., in patients with cystic fibrosis, including pulmonary exacerbations due to bacterial infections in same. The methods of treating disclosed herein comprise the steps of administering to the subject a therapeutically effective amount of an IL-17F antagonist.

In one embodiment, the present invention provides a method of diagnosing a disorder related to IL-17F in a subject, comprising the steps of detecting a test amount of an IL-17F gene product in a sample from the subject; and comparing the test amount with a normal amount of the IL-17F gene product in a control sample, whereby a test amount significantly above the normal amount provides a positive indication in the diagnosis of a disorder related to IL-17F. In another embodiment, the disorder related to IL-17F is airway inflammation. In another embodiment, the subject is a patient diagnosed with cystic fibrosis. In another embodiment, the subject is undergoing a pulmonary exacerbation. In a further embodiment, the pulmonary exacerbation is due to an infectious agent. In another embodiment, the IL-17F gene product is an IL-17F protein. In a further embodiment, the IL-17F protein is detected with an anti-IL-17F antibody.

In another embodiment, the invention provides a method of screening for compounds capable of inhibiting IL-17F binding to IL-17R comprising the steps of contacting a sample containing IL-17F and IL-17R with a compound; and determining whether the binding of IL-17F to IL-17R in the sample contacted with the test compound is decreased relative to the binding of IL-17F to IL-17R in a sample not contacted with the compound, whereby a decrease in the binding of IL-17F to IL-17R in the sample contacted with the compound identifies the compound as one that inhibits IL-17F binding to IL-17R.

In another embodiment, the invention provides a method of treating a subject at risk for, or diagnosed with, a disorder related to IL-17F comprising administering to the subject a therapeutically effective amount of an IL-17F antagonist. In another embodiment, the disorder related to IL-17F is airway inflammation. In another embodiment, the subject is a patient diagnosed with cystic fibrosis. In another embodiment, the subject is undergoing a pulmonary exacerbation. In a further embodiment, the pulmonary exacerbation is due to an infectious agent. In another embodiment, the IL-17F antagonist is selected from the group consisting of an inhibitory anti-IL-17F antibody, an inhibitory anti-IL-17R antibody, soluble IL-17R, a fusion protein containing IL-17R, a fusion protein containing an IL-17F binding fragment of IL-17R, an antagonistic small molecule, an antisense IL-17F nucleic acid molecule, an antisense IL-17R nucleic acid molecule, an siRNA IL-17F nucleic acid molecule, and an siRNA IL-17R nucleic acid molecule. In another embodiment, the invention further comprises administering to the subject a therapeutically effective amount of at least one additional therapeutic agent. In a further embodiment, the at least one additional therapeutic agent is selected from the group consisting of cytokine inhibitors, growth factor inhibitors, immunosuppressants, anti-inflammatory agents, metabolic inhibitors, enzyme inhibitors, cytotoxic agents, and cytostatic agents. In another further embodiment, the at least one additional therapeutic agent is selected from the group consisting of TNF antagonists, anti-TNF agents, IL-12 antagonists, IL-15 antagonists, IL-17 antagonists, IL-18 antagonists, IL-22 antagonists, T cell-depleting agents, B cell-depleting agents, cyclosporin, FK-506, CCI-779, etanercept, infliximab, rituximab, adalimumab, prednisolone, azathioprine, gold, sulphasalazine, chloroquine, hydroxychloroquine, minocycline, anakinra, abatacept, methotrexate, leflunomide, rapamycin, rapamycin analogs, Cox-2 inhibitors, cPLA2 inhibitors, NSAIDs, p38 inhibitors, antagonists of B7.1, B7.2, ICOSL, ICOS and/or CD28, and agonists of CTLA4.

In another embodiment, the invention provides a pharmaceutical composition comprising an IL-17F antagonist and a pharmaceutically acceptable carrier. In another embodiment, the IL-17F antagonist is selected from the group consisting of an inhibitory anti-IL-17F antibody, an inhibitory anti-IL-17R antibody, soluble IL-17R, a fusion protein containing IL-17R, a fusion protein containing an IL-17F binding fragment of IL-17R, an antagonistic small molecule, an antisense IL-17F nucleic acid molecule, an antisense IL-17R nucleic acid molecule, an siRNA IL-17F nucleic acid molecule, and an siRNA IL-17R nucleic acid molecule.

In another embodiment, the invention provides a vaccine adjuvant comprising an IL-17F antagonist and a bacterial antigen. In another embodiment, the IL-17F antagonist is selected from the group consisting of an inhibitory anti-IL-17F antibody, an inhibitory IL-17R antibody, soluble IL-17R, a fusion protein containing IL-17R, a fusion protein containing an IL-17F binding fragment of IL-17R, an antagonistic small molecule, an antisense IL-17F nucleic acid molecule, an antisense IL-17R nucleic acid molecule, an siRNA IL-17F nucleic acid molecule, and an siRNA IL-17R nucleic acid molecule.

BRIEF DESCRIPTION OF THE DRAWINGS

Concentrations (fold change compared to control media; y-axis) of GRO-α, G-CSF and MCP-1 protein levels in basolateral media collected from primary human bronchial epithelial (HBE) cells treated for 24 hours with 1 ng/ml, 10 ng/ml, or 100 ng/ml (x-axis) of either IL-17A (■) or IL-17F (□) are shown in FIG. 1 (left panels). Shown in FIG. 1 (right panels) are concentrations (pg/ml; y-axis) of GRO-α, G-CSF, and MCP-1 in basolateral media collected from HBE cells stimulated with 10 ng/ml of either IL-17A (■) or IL-17F (□) for 4, 8, 16 or 24 hrs (x-axis). Results are expressed as the mean±SEM of triplicate samples from one representative experiment.

Shown in FIG. 2 are concentrations (fold change compared to control media; y-axis) of A) GRO-α in basolateral media collected from primary HBE cells treated with one of the four following conditions (x-axis): IL-17F (10 ng/ml), TNF-α (1 ng/ml), IL-17F (10 ng/ml)+TNF-α (1 ng/ml), or IL-17F+TNF-α preincubated with an anti-IL-17R mAb, B) G-CSF in basolateral media collected from primary HBE cells treated with one of the four following conditions (x-axis): IL-17F (10 ng/ml), TNF-α (1 ng/ml), IL-17F (10 ng/ml)+TNF-α (1 ng/ml), IL-17F+TNF-α preincubated with IL-17R-Fc (1 μg/ml) or IL-17F+TNF-α preincubated with an anti-IL-17R mAb, or C) G-CSF in basolateral media collected from primary HBE cells treated with one of the four following conditions (x-axis): IL-17A (10 ng/ml), TNF-α (1 ng/ml), IL-17A (10 ng/ml)+TNF-α (1 ng/ml), IL-17A+TNF-α preincubated with IL-17R-Fc (1 μg/ml), or IL-17A+TNF-α preincubated with an anti-IL-17R mAb. Results are expressed as the mean±SEM of three separate experiments (* denotes $p<0.05$ by ANOVA).

Figure 5:
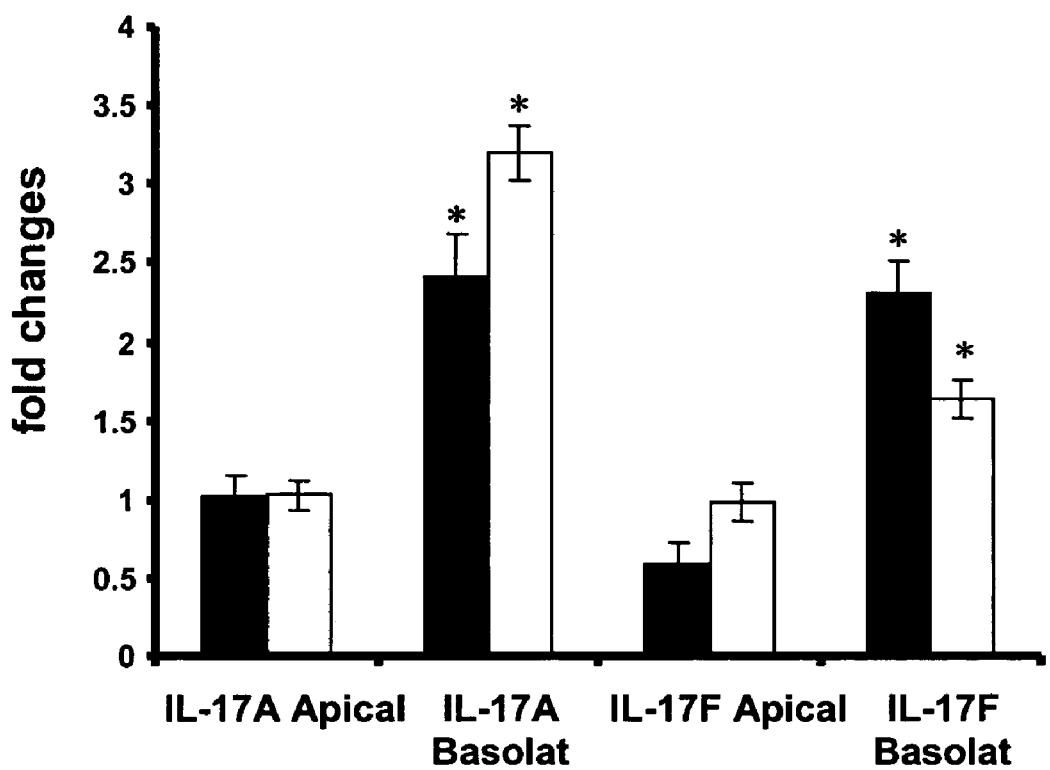

Shown in FIG. 5 are G-CSF (■) and GRO-α (□) concentrations (fold change compared to control; y-axis) by primary HBE cells after addition of 10 ng/ml of either IL-17A or IL-17F to basolateral or apical surface. Results are expressed as the mean±SEM of triplicate samples from one representative experiment (* denotes $p<0.05$ by ANOVA).

Figure 6:
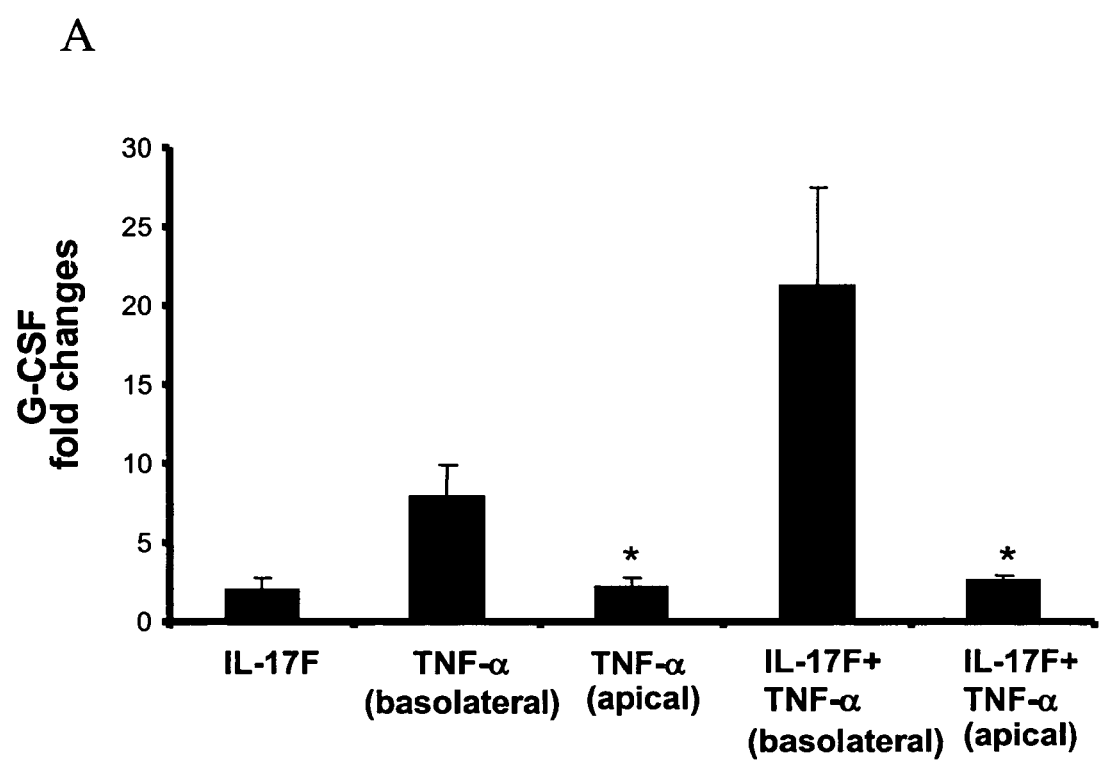
Figure 6:
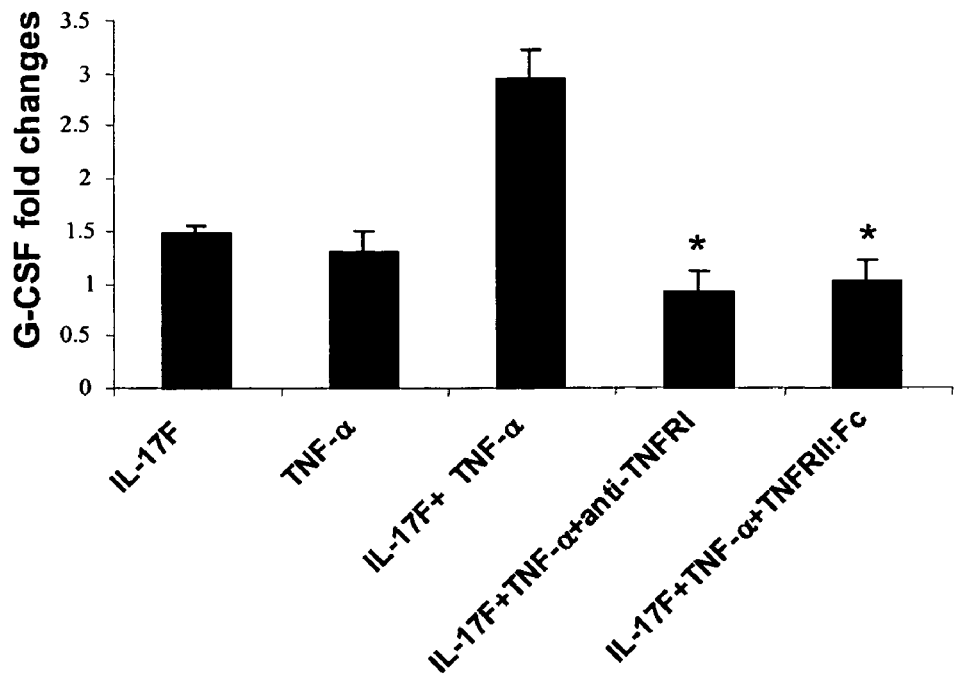
Figure 6:
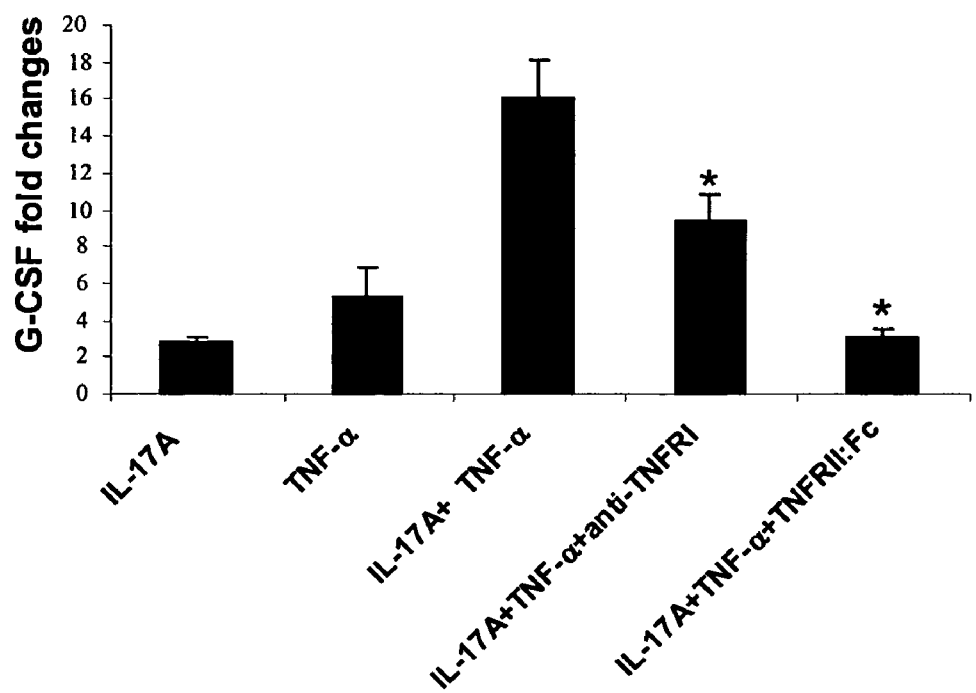

FIG. 6 shows the shows the concentrations (fold change compared to control media; y-axis) of G-CSF in A) apical or basolateral media collected from primary HBE cells that were treated with 10 ng/ml IL-17F and/or 10 ng/ml TNF-α (x-axis) for 24 hours, B) basolateral media collected from primary HBE cells pretreated with anti-human TNF-RI and/or TNF-RII:Fc chimera (0.5 μg/ml) 2 hours prior to 24 hour incubation with either 10 ng/ml IL-17F and/or 10 ng/ml TNF-α, or C) basolateral media collected from primary HBE cells pretreated with anti human TNF-RI and/or TNF-RII:Fc chimera (0.5 μg/ml) 2 hours prior to 24 hour incubation with either 10 ng/ml IL-17A and/or 10 ng/ml TNF-α. Results are expressed as the mean±SEM of three separate experiments (* denotes $p<0.05$ by ANOVA).

Figure 7A:
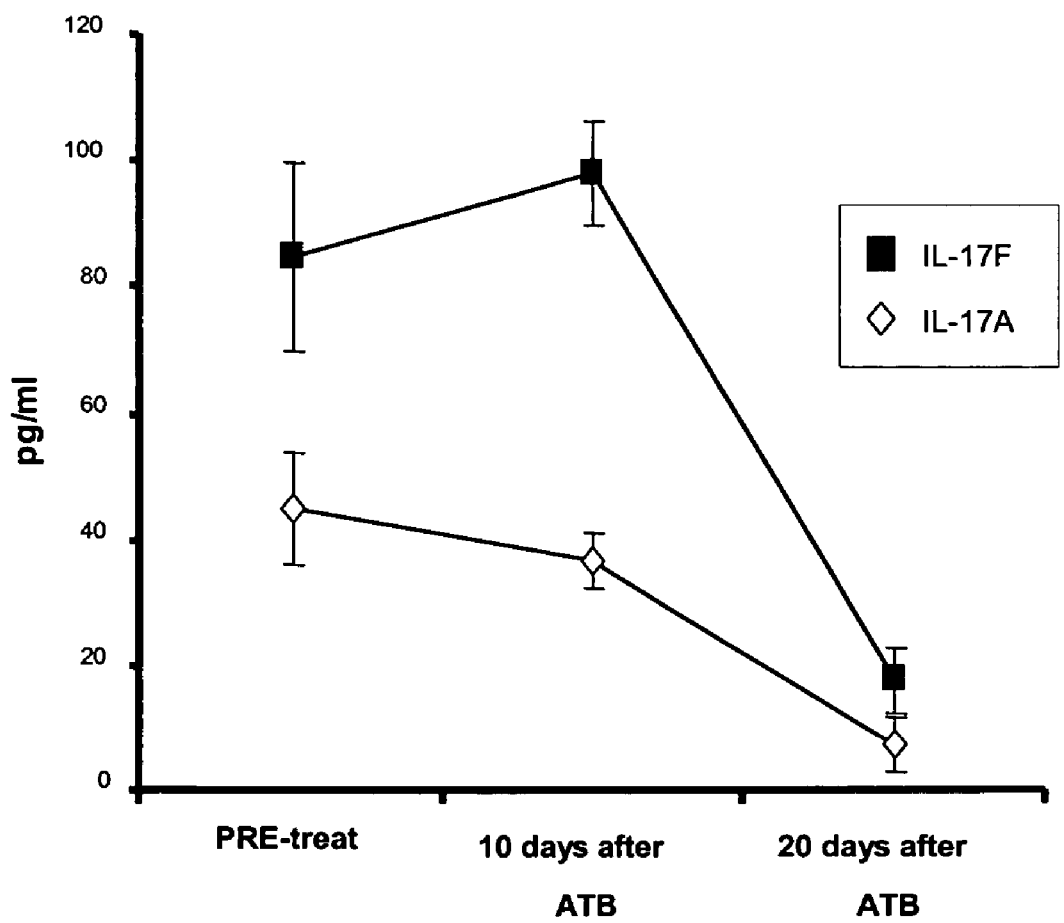
Figure 7B:
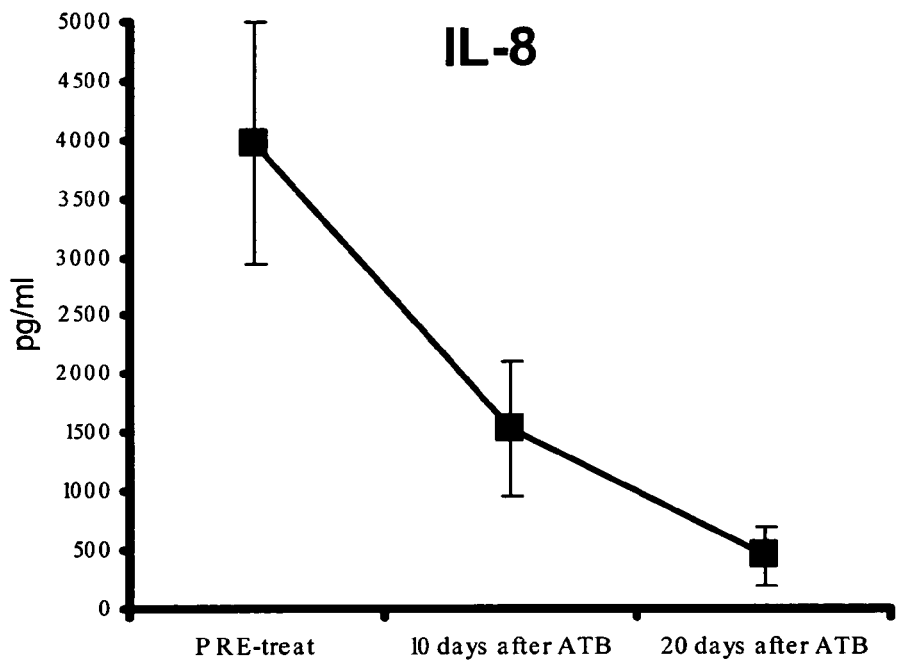
Figure 7B:
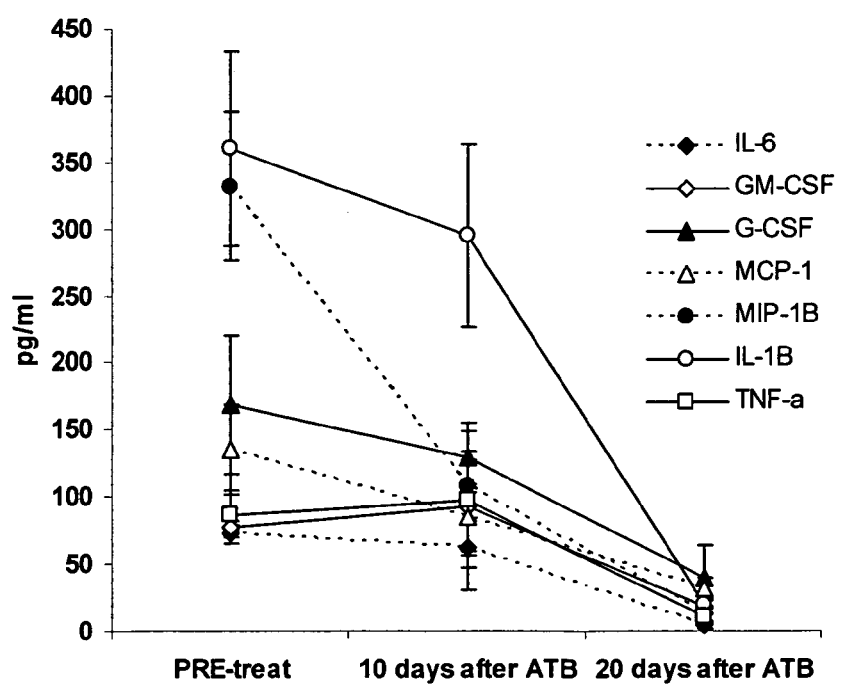

FIG. 7 shows concentrations (pg/ml; y-axes) of A) IL-17A and IL-17F, and B) (upper panel) IL-8, and (lower panel) IL-6, GM-CSF, G-CSF, MCP-1, MIP-1β, IL-1β, and TNF-α in sputum samples obtained from patients with cystic fibrosis who are suffering from pulmonary exacerbation prior to treatment (PRE-treat), 10 days after antibiotic treatment (ATB), or 20 days after ATB.

DETAILED DESCRIPTION OF THE INVENTION

The present invention is based, in part, on the following findings: 1) IL-17R is expressed at the greatest level on the basolateral surfaces of respiratory epithelial cells, 2) IL-17F is more potent in stimulating expression of inflammatory cytokines, chemokines, and/or growth factors when supplied to respiratory epithelial cells basolaterally compared to when it is supplied apically, 3) IL-17F-mediated induction of cytokines, chemokines, and/or growth factors is significantly attenuated by an inhibitory anti-IL-17R antibody, and 4) IL-17F expression levels correlate with the progress of airway inflammation, e.g., in patients with cystic fibrosis, including pulmonary exacerbations due to bacterial infections in same. These findings strongly support a role for IL-17F, and its subsequent signaling through IL-17R, in inflammatory disorders of the respiratory system.

As such, the present invention relates to IL-17F and IL-17R polynucleotides and polypeptides, and uses thereof. Such uses include, but are not limited to, the generation of specific antibodies, which may then be used in methods of screening test compounds capable of inhibiting, i.e., decreasing, limiting, blocking, or otherwise reducing, IL-17F binding to IL-7R, methods of monitoring expression levels in a sample or subject (e.g., to diagnose, prognose, and/or monitor), and methods of treating airway inflammation, e.g., in patients with cystic fibrosis, including pulmonary exacerbations due to bacterial infections in same.

Polynucleotides and Polypeptides of IL-17F and IL-17R

IL-17F nucleotide and amino acid sequences are known in the art and are provided. The nucleotide sequence of human IL-17F is set forth as SEQ ID NO:1. The amino acid sequence of full-length IL-17F protein corresponding to the foregoing nucleotide sequence is set forth as SEQ ID NO:2. The amino acid sequence of mature IL-17F corresponds to a protein beginning at about amino acid 31 of SEQ ID NO:2 (see, e.g., U.S. patent application Ser. No. 10/102,080, incorporated herein in its entirety by reference).

IL-17R nucleotide and amino acid sequences are known in the art and are provided. The nucleotide sequence of human IL-17R is set forth as SEQ ID NO:3, which includes a poly(A) tail. The amino acid sequence of full-length IL-17R protein corresponding to the foregoing nucleotide sequence is set forth as SEQ ID NO:4.

The nucleic acids related to the present invention may comprise DNA or RNA and may be wholly or partially synthetic. Reference to a nucleotide sequence as set out herein encompasses a DNA molecule with the specified sequence, and encompasses an RNA molecule with the specified sequence in which U is substituted for T, unless context requires otherwise.

The isolated polynucleotides related to the present invention may be used as hybridization probes and primers to identify and isolate nucleic acids having sequences identical to or similar to those encoding the disclosed polynucleotides. Hybridization methods for identifying and isolating nucleic acids include polymerase chain reaction (PCR), Southern hybridizations, in situ hybridization and Northern hybridization, and are well known to those skilled in the art.

Hybridization reactions may be performed under conditions of different stringency. The stringency of a hybridization reaction includes the difficulty with which any two nucleic acid molecules will hybridize to one another. Preferably, each hybridizing polynucleotide hybridizes to its corresponding polynucleotide under reduced stringency conditions, more preferably stringent conditions, and most preferably highly stringent conditions. Examples of stringency conditions are shown in Table 1 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 1

Stringency Conditions

| Stringency Condition | Polynucleotide Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B^*$; 1xSSC | $T_B^*$; 1xSSC |
| C | DNA:RNA | >50 | 67° C.; 1xSSC -or- 45° C.; 1xSSC, 50% formamide | 67° C.; 0.3xSSC |
| D | DNA:RNA | <50 | $T_D^*$; 1xSSC | $T_D^*$; 1xSSC |
| E | RNA:RNA | >50 | 70° C.; 1xSSC -or- 50° C.; 1xSSC, 50% formamide | 70° C.; 0.3xSSC |
| F | RNA:RNA | <50 | $T_F^*$; 1xSSC | $T_F^*$; 1xSSC |
| G | DNA:DNA | >50 | 65° C.; 4xSSC -or- 42° C.; 4xSSC, 50% formamide | 65° C.; 1xSSC |
| H | DNA:DNA | <50 | $T_H^*$; 4xSSC | $T_H^*$; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J^*$; 4xSSC | $T_J^*$; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L^*$; 2xSSC | $T_L^*$; 2xSSC |
| M | DNA:DNA | >50 | 50° C.; 4xSSC -or- 40° C.; 6xSSC, 50% formamide | 50° C.; 2xSSC |
| N | DNA:DNA | <50 | $T_N^*$; 6xSSC | $T_N^*$; 6xSSC |
| O | DNA:RNA | >50 | 55° C.; 4xSSC -or- 42° C.; 6xSSC, 50% formamide | 55° C.; 2xSSC |
| P | DNA:RNA | <50 | $T_P^*$; 6xSSC | $T_P^*$; 6xSSC |
| Q | RNA:RNA | >50 | 60° C.; 4xSSC -or- 45° C.; 6xSSC, 50% formamide | 60° C.; 2xSSC |
| R | RNA:RNA | <50 | $T_R^*$; 4xSSC | $T_R^*$; 4xSSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[2]SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}Na^+$) + 0.41(% G + C) − (600/N), where N is the number of bases in the hybrid, and $Na^+$ is the concentration of sodium ions in the hybridization buffer ($Na^+$ for 1xSSC = 0.165M).
Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, NY, chapters 9 and 11, and Current Protocols in Molecular Biology, 1995, F. M. Ausubel et al., eds., John Wiley & Sons, Inc., sections 2.10 and 6.3-6.4, incorporated herein by reference.

The isolated polynucleotides related to the present invention may be used as hybridization probes and primers to identify and isolate DNA having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least 90% sequence identity (more preferably, at least 95% identity; most preferably, at least 99% identity) with the disclosed polynucleotides. Alternatively, significant similarity exists when the nucleic acid segments will hybridize under selective hybridization conditions (e.g., highly stringent hybridization conditions) to the disclosed polynucleotides.

The isolated polynucleotides related to the present invention may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least 50% sequence identity (more preferably, at least 75% identity; most preferably, at least 90% identity) with the disclosed polynucleotides, whereas polypeptide homologs have at least 30% sequence identity (more preferably, at least 45% identity; most preferably, at least 60% identity) with the disclosed polypeptides. Preferably, homologs of the disclosed polynucleotides and polypeptides are those isolated from mammalian species.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and nonhomologous sequences can be disregarded for comparison purposes).

In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent sequence identity between two sequences may be accomplished using a mathematical algorithm. In a preferred embodiment, the percent identity between two amino acid sequences is determined using the Needleman and Wunsch ((1970) *J. Mol. Biol.* 48:444-53) algorithm, which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is a Blossum 62 scoring matrix with a gap penalty of 12, a gap extend penalty of 4, and a frameshift gap penalty of 5. The percent identity between two amino acid or nucleotide sequences can also be determined using the algorithm of Meyers and Miller ((1989) *CABIOS* 4:11-17), which has been incorporated into the ALIGN program (version 2.0), using a PAM120 weight residue table, a gap length penalty of 12 and a gap penalty of 4.

The isolated polynucleotides related to the present invention may also be used as hybridization probes and primers to identify cells and tissues that express the polypeptides related to the present invention and the conditions under which they are expressed.

Additionally, the function of the polypeptides related to the present invention may be directly examined by using the polynucleotides encoding the polypeptides to alter (i.e., enhance, reduce, or modify) the expression of the genes corresponding to the polynucleotides related to the present invention in a cell or organism. These "corresponding genes" are the genomic DNA sequences related to the present invention that are transcribed to produce the mRNAs from which the polynucleotides related to the present invention are derived.

Altered expression of the genes related to the present invention may be achieved in a cell or organism through the use of various inhibitory polynucleotides, such as antisense polynucleotides and ribozymes that bind and/or cleave the mRNA transcribed from the genes related to the invention (see, e.g., Galderisi et al. (1999) *J. Cell Physiol.* 181:251-57; Sioud (2001) *Curr. Mol. Med.* 1:575-88). An inhibitory polynucleotide(s), e.g., to IL-17F and/or IL-17R, may be used as an antagonist, e.g., to inhibit IL-17F binding to IL-17R. Consequently, such inhibitory polynucleotides may be useful in preventing or treating disorders related IL-17F binding to IL-17R, e.g., airway inflammation, e.g., in patients with cystic fibrosis, including pulmonary exacerbations due to bacterial infections in same.

The antisense polynucleotides or ribozymes related to the invention may be complementary to an entire coding strand of a gene related to the invention, or to only a portion thereof. Alternatively, antisense polynucleotides or ribozymes can be complementary to a noncoding region of the coding strand of a gene related to the invention. The antisense polynucleotides or ribozymes can be constructed using chemical synthesis and enzymatic ligation reactions using procedures well known in the art. The nucleoside linkages of chemically synthesized polynucleotides can be modified to enhance their ability to resist nuclease-mediated degradation, as well as to increase their sequence specificity. Such linkage modifications include, but are not limited to, phosphorothioate, methylphosphonate, phosphoroamidate, boranophosphate, morpholino, and peptide nucleic acid (PNA) linkages (Galderisi et al., supra; Heasman (2002) *Dev. Biol.* 243:209-14; Micklefield (2001) *Curr. Med. Chem.* 8:1157-79). Alternatively, these molecules can be produced biologically using an expression vector into which a polynucleotide related to the present invention has been subcloned in an antisense (i.e., reverse) orientation.

The inhibitory polynucleotides of the present invention also include triplex-forming oligonucleotides (TFOs) that bind in the major groove of duplex DNA with high specificity and affinity (Knauert and Glazer (2001) *Hum. Mol. Genet.* 10:2243-51). Expression of the genes related to the present invention can be inhibited by targeting TFOs complementary to the regulatory regions of the genes (i.e., the promoter and/or enhancer sequences) to form triple helical structures that prevent transcription of the genes.

In one embodiment of the invention, the inhibitory polynucleotides of the present invention are short interfering RNA (siRNA) molecules. These siRNA molecules are short (preferably 19-25 nucleotides; most preferably 19 or 21 nucleotides), double-stranded RNA molecules that cause sequence-specific degradation of target mRNA. This degradation is known as RNA interference (RNAi) (see, e.g., Bass (2001) *Nature* 411:428-29). Originally identified in lower organisms, RNAi has been effectively applied to mammalian cells and has recently been shown to prevent fulminant hepatitis in mice treated with siRNA molecules targeted to Fas mRNA (Song et al. (2003) *Nature Med.* 9:347-51). In addition, intrathecally delivered siRNA has recently been reported to block pain responses in two models (agonist-induced pain model and neuropathic pain model) in the rat (Dorn et al. (2004) *Nucleic Acids Res.* 32(5):e49).

The siRNA molecules of the present invention may be generated by annealing two complementary single-stranded RNA molecules together (one of which matches a portion of the target mRNA) (Fire et al., U.S. Pat. No. 6,506,559) or through the use of a single hairpin RNA molecule that folds back on itself to produce the requisite double-stranded portion (Yu et al. (2002) *Proc. Natl. Acad. Sci. USA* 99:6047-52). The siRNA molecules may be chemically synthesized (Elbashir et al. (2001) *Nature* 411:494-98) or produced by in vitro transcription using single-stranded DNA templates (Yu et al., supra). Alternatively, the siRNA molecules can be produced biologically, either transiently (Yu et al., supra; Sui et al. (2002) *Proc. Natl. Acad. Sci. USA* 99:5515-20) or stably (Paddison et al. (2002) *Proc. Natl. Acad. Sci. USA* 99:1443-48), using an expression vector(s) containing the sense and antisense siRNA sequences. Recently, reduction of levels of target mRNA in primary human cells, in an efficient and sequence-specific manner, was demonstrated using adenoviral vectors that express hairpin RNAs, which are further processed into siRNAs (Arts et al. (2003) *Genome Res.* 13:2325-32).

The siRNA molecules targeted to the polynucleotides related to the present invention can be designed based on criteria well known in the art (e.g., Elbashir et al. (2001) *EMBO J.* 20:6877-88). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; and the target segment preferably should be in the ORF region of the target mRNA and preferably should be at least 75 bp after the initiation ATG and at least 75 bp before the stop codon. Based on these criteria, or on other known criteria (e.g., Reynolds et al. (2004) *Nature Biotechnol.* 22:326-30), siRNA molecules related to the present invention that target the mRNA polynucleotides related to the present invention may be designed by one of ordinary skill in the art.

Altered expression of the genes related to the present invention in an organism may also be achieved through the creation of nonhuman transgenic animals into whose genomes polynucleotides related to the present invention have been introduced. Such transgenic animals include animals that have multiple copies of a gene (i.e., the transgene) of the present invention. A tissue-specific regulatory sequence(s) may be operably linked to the transgene to direct expression of a polypeptide related to the present invention to particular cells or a particular developmental stage. Methods for generating transgenic animals via embryo manipulation and microinjection, particularly animals such as mice, have become conventional and are well known in the art (e.g., Bockamp et al., *Physiol. Genomics,* 11:115-32 (2002)).

Altered expression of the genes related to the present invention in an organism may also be achieved through the creation of animals whose endogenous genes corresponding to the polynucleotides related to the present invention have been disrupted through insertion of extraneous polynucleotide sequences (i.e., a knockout animal). The coding region of the endogenous gene may be disrupted, thereby generating a nonfunctional protein. Alternatively, the upstream regulatory region of the endogenous gene may be disrupted or replaced with different regulatory elements, resulting in the altered expression of the still-functional protein. Methods for generating knockout animals include homologous recombination and are well known in the art (e.g., Wolfer et al., *Trends Neurosci.,* 25:336-40 (2002)).

The isolated polynucleotides of the present invention also may be operably linked to an expression control sequence and/or ligated into an expression vector for recombinant production of the polypeptides (including active fragments and/or fusion polypeptides thereof) related to the present invention. General methods of expressing recombinant proteins are well known in the art.

An expression vector, as used herein, is intended to refer to a nucleic acid molecule capable of transporting another nucleic acid to which it has been linked. One type of vector is a plasmid, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as recombinant expression vectors (or simply, expression vectors). In general, expression vectors of utility in recombinant DNA techniques are often in the form of plasmids. In the present specification, plasmid and vector may be used interchangeably as the plasmid is the most commonly used form of vector. However, the invention is intended to include other forms of expression vectors, such as viral vectors (e.g., replication defective retroviruses, adenoviruses and adeno-associated viruses), that serve equivalent functions.

In one embodiment, the polynucleotides related to the present invention are used to create recombinant IL-17F agonists, e.g., those that can be identified based on the presence of at least one "IL-17F receptor-binding motif." As used herein, the term "IL-17F receptor-binding motif" includes amino acid sequences or residues that are important for binding of IL-17F to its requisite receptor. Examples of an IL-17F agonist include recombinant IL-17F, and/or fragments thereof, e.g., IL-17R binding fragments thereof. In another embodiment, the polynucleotides related to the present invention are used to create IL-17F antagonists (e.g., IL-17F and/or IL-17R inhibitory polynucleotides; soluble IL-17R polypeptides (including fragments (e.g., IL-17F binding fragments) and/or fusion proteins thereof); inhibitory anti-IL-17F or anti-IL-17R antibodies; and/or antagonistic small molecules, etc.).

Methods of creating fusion polypeptides, i.e., a first polypeptide moiety linked with a second polypeptide moiety, are well known in the art. For example, an IL-17F polypeptide or IL-17R polypeptide, including fragments thereof, may be fused to a second polypeptide moiety, e.g., an immunoglobulin or a fragment thereof (e.g., an Fc-binding fragment thereof). In some embodiments, the first polypeptide moiety includes, e.g., full-length IL-17F or IL-17R polypeptide. Alternatively, the first polypeptide may comprise less than the full-length IL-17F or IL-17R polypeptide. Additionally, soluble forms of e.g., IL-17F or IL-17R may be fused through "linker" sequences to the Fc portion of an immunoglobulin. Other fusions proteins, such as those incorporating glutathione-S-transferase (GST), Lex-A, thioredoxin (TRX) or maltose-binding protein (MBP), may also be used.

The second polypeptide moiety is preferably soluble. In some embodiments, the second polypeptide moiety enhances the half-life, (e.g., the serum half-life) of the linked polypeptide. In some embodiments, the second polypeptide moiety includes a sequence that facilitates association of the fusion polypeptide with a second IL-17F or IL-17R polypeptide. In preferred embodiments, the second polypeptide includes at least a region of an immunoglobulin polypeptide. Immunoglobulin fusion polypeptide are known in the art and are described in, e.g., U.S. Pat. Nos. 5,516,964; 5,225,538; 5,428,130; 5,514,582; 5,714,147; and 5,455,165, all of which are hereby incorporated by reference herein. The fusion proteins may additionally include a linker sequence joining the first polypeptide moiety, e.g., IL-17F or IL-17R, including fragments thereof, to the second moiety. Use of such linker sequences are well known in the art. For example, the fusion protein can include a peptide linker, e.g., a peptide linker of about 2 to 20, more preferably less than 10, amino acids in length. In one embodiment, the peptide linker may be 2 amino acids in length.

In another embodiment, the recombinant protein includes a heterologous signal sequence (i.e., a polypeptide sequence that is not present in a polypeptide encoded by an IL-17F or IL-17R nucleic acid) at its N-terminus. For example, a signal sequence from another protein may be fused with an IL-17F or IL-17R polypeptide, including fragments and/or fusion proteins thereof. In certain host cells (e.g., mammalian host cells), expression and/or secretion of recombinant proteins can be increased through use of a heterologous signal sequence. A signal peptide that may be included in the fusion protein is the melittin signal peptide MKFLVNVALVFMV-VYISYIYA (SEQ ID NO:5).

A fusion protein of the invention may be produced by standard recombinant DNA techniques. For example, DNA fragments coding for the different polypeptide sequences are ligated together in-frame in accordance with conventional techniques by employing, e.g., blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments may be carried out using anchor primers that give rise to complementary overhangs between two consecutive gene fragments that can subsequently be annealed and reamplified to generate a chimeric gene sequence (see, for example, Ausubel et al. (Eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). An IL-17F- or IL-17R-encoding nucleic acid may be cloned into such an expression vector such that the fusion moiety is linked in-frame to the immunoglobulin protein. In some embodiments, IL-17F or IL-17R fusion polypeptides exist as oligomers, such as dimers or trimers.

The recombinant expression vectors of the invention may carry additional sequences, such as sequences that regulate replication of the vector in host cells (e.g., origins of replication) and selectable marker genes. The selectable marker gene facilitates selection of host cells into which the vector has been introduced. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Suitable vectors can be chosen or constructed, containing appropriate regulatory sequences, including promoter sequences, terminator sequences, polyadenylation sequences, enhancer sequences, marker genes and other sequences, e.g., sequences that regulate replication of the vector in the host cells (e.g., origins of replication) as appropriate. Vectors may be plasmids or viral, e.g., phage, or phagemid, as appropriate. For further details see, for example, Molecular Cloning: a Laboratory Manual: 2nd ed., Sambrook et al., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd ed., Ausubel et al. eds., John Wiley & Sons, 1992.

Thus, a further aspect of the present invention provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection, and transduction using retrovirus or other viruses, e.g., vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g., by culturing host cells under conditions for expression of the gene.

A number of cell lines may act as suitable host cells for recombinant expression of the polypeptides related to the present invention. Mammalian host cell lines include, for example, COS cells, CHO cells, 293 cells, A431 cells, 3T3 cells, CV-1 cells, HeLa cells, L cells, BHK21 cells, HL-60 cells, U937 cells, HaK cells, Jurkat cells, as well as cell strains derived from in vitro culture of primary tissue and primary explants.

Alternatively, it should be possible to recombinantly produce the polypeptides related to the present invention in lower eukaryotes, such as yeast, or in prokaryotes. Potentially suitable yeast strains include *Saccharomyces cerevisiae*, *Schizosaccharomyces pombe*, *Kluyveromyces* strains, and *Candida* strains. Potentially suitable bacterial strains include *Escherichia coli*, *Bacillus subtilis*, and *Salmonella typhimurium*. If the polypeptides related to the present invention are made in yeast or bacteria, it may be necessary to modify them by, for example, phosphorylation or glycosylation of appropriate sites, in order to obtain functionality. Such covalent attachments may be accomplished using well-known chemical or enzymatic methods.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment that allows correct formation of disulfide bonds (a redox system). General methods of refolding are disclosed in Kohno (1990) *Meth. Enzymol.* 185:187-95. EP 0433225, and U.S. Pat. No. 5,399,677 describe other appropriate methods.

The polypeptides related to the present invention may also be recombinantly produced by operably linking the isolated polynucleotides of the present invention to suitable control sequences in one or more insect expression vectors, such as baculovirus vectors, and employing an insect cell expression system. Materials and methods for baculovirus/Sf9 expression systems are commercially available in kit form (e.g., the MaxBac® kit, Invitrogen, Carlsbad, Calif.).

Following recombinant expression in the appropriate host cells, the recombinant polypeptides of the present invention may then be purified from culture medium or cell extracts using known purification processes, such as gel filtration and ion exchange chromatography. For example, IL-17F or IL-17R protein (including fragments and/or fusion proteins thereof) may be purified from conditioned media. Membrane-bound forms of; e.g., IL-17R, may be purified by preparing a total membrane fraction from the expressing cell and extracting the membranes with a nonionic detergent such as Triton X-100. A polypeptide related to the present invention may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of recombinant proteins from culture supernatant may also include one or more column steps over such affinity resins as concanavalin A-agarose, heparin-TOYOPEARL® (Toyo Soda Manufacturing Co., Ltd., Japan) or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the recombinant protein. Affinity columns including antibodies (e.g., those described using the methods herein) to the recombinant protein may also be used in purification in accordance with known methods. Some or all of the foregoing purification steps, in various combinations or with other known methods, may also be employed to provide a substantially purified isolated recombinant protein. Preferably, the isolated recombinant protein is purified so that it is substantially free of other mammalian proteins. Additionally, these purification processes may also be used to purify the polypeptides of the present invention from other sources, including natural sources. For example, polypeptides related to the invention, e.g., IL-17F or IL-17R polypeptides (including fragments and/or fusion proteins thereof), which are expressed as a product of transgenic animals, e.g., as a component of the milk of transgenic cows, goats, pigs, or sheep, may be purified as described above.

Alternatively, the polypeptides may also be recombinantly expressed in a form that facilitates purification. For example, the polypeptides may be expressed as fusions with proteins such as maltose-binding protein (MBP), glutathione-S-transferase (GST), or thioredoxin (TRX). Kits for expression and purification of such fusion proteins are commercially available from New England BioLabs (Beverly, Mass.), Pharmacia (Piscataway, N.J.), and Invitrogen, respectively. Recombinant proteins can also be tagged with a small epitope and subsequently identified or purified using a specific antibody to the epitope. A preferred epitope is the FLAG epitope, which is commercially available from Eastman Kodak (New Haven, Conn.).

The polypeptides related to the present invention may also be produced by known conventional chemical synthesis. Methods for chemically synthesizing such polypeptides are well known to those skilled in the art. Such chemically synthetic polypeptides may possess biological properties in common with the natural, purified polypeptides, and thus may be employed as biologically active or immunological substitutes for the natural polypeptides.

The polypeptides related to the present invention also encompass molecules that are structurally different from the disclosed polypeptides (e.g., have a slightly altered sequence), but have substantially the same biochemical properties as the disclosed polypeptides (e.g., are changed only in functionally nonessential amino acid residues). Such molecules include naturally occurring allelic variants and deliberately engineered variants containing alterations, substitutions, replacements, insertions, or deletions. Techniques for such alterations, substitutions, replacements, insertions, or deletions are well known to those skilled in the art. In some embodiments, the polypeptide moiety is provided as a variant polypeptide having mutations in the naturally occurring sequence (wild type) that results in a sequence more resistant to proteolysis (relative to the nonmutated sequence).

IL-17F or IL-17R polypeptides, and fragments and/or fusion polypeptides thereof, may be used to screen agents that are capable of binding IL-17F and/or inhibiting IL-17F bioactivity, i.e., antagonistic agents. Such antagonists, e.g., inhibitory polynucleotides, polypeptides (including fragments and fusion proteins thereof), antibodies, small compounds, etc., may inhibit IL-17F bioactivity, e.g., by inhibiting IL-17F binding to IL-17R. Binding assays utilizing a desired binding protein, immobilized or not, are well known in the art and may be used for this purpose with the polypeptides related to the present invention, including IL-17R. Purified cell-based or protein-based (cell-free) screening assays may be used to identify such agents. For example, IL-17F protein may be immobilized in purified form on a carrier and binding of potential ligands to purified IL-17F may be measured.

Antibodies

The inventors used anti-IL-17F antibodies (i.e., intact antibodies and antigen binding fragments thereof) that specifically bind to IL-17F to detect IL-17F in sputum samples collected from patients with cystic fibrosis who also suffered from pulmonary exacerbation. Additionally, the inventors used a monoclonal antibody specific for IL-17R to antagonize IL-17F-mediated production of inflammatory cytokines (e.g., GRO-α and G-CSF). Thus, in one embodiment of the invention, antagonistic anti-IL-17F or anti-IL-17R antibodies may be useful in diagnosing, prognosing, monitoring and/or treating disorders related to IL-17F, e.g., airway inflammation, e.g., in patients with cystic fibrosis, including pulmonary exacerbations due to bacterial infections in same. The antibodies may be human, humanized, chimeric, or in vitro-generated antibodies.

One of skill in the art will recognize that, as used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDRs") interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242; and Chothia et al. (1987) J. Mol. Biol. 196:901-17, which are hereby incorporated by reference). Each VH and VL is composed of three CDRs and four FRs, arranged from amino-terminus to carboxy-terminus in the following order: FR1, CDR1, FR2, CDR2, FR3, CDR3, FR4.

The antibody may further include a heavy and light chain constant region to thereby form a heavy and light immunoglobulin chain, respectively. In one embodiment, the antibody is a tetramer of two heavy immunoglobulin chains and two light immunoglobulin chains, wherein the heavy and light immunoglobulin chains are interconnected, e.g., by disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

Immunoglobulin refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd, or 214 amino acids) are encoded by a variable region gene at the $NH_2$-terminus (about 110 amino acids) and a kappa or lambda constant region gene at the COOH-terminus. Full-length immunoglobulin "heavy chains" (about 50 Kd, or 446 amino acids), are similarly encoded by a variable region gene (about 116 amino acids) and one of the other aforementioned constant region genes, e.g., gamma (encoding about 330 amino acids). The immunoglobulin heavy chain constant region genes encode for the antibody class, i.e., isotype (e.g., IgM or IgG1). The antigen binding fragment of an antibody (or simply "antibody portion," or "fragment"), as used herein, refers to one or more fragments of a full-length antibody that retain the ability to specifically bind to an antigen (e.g., CD3). Examples of binding fragments encompassed within the term "antigen binding fragment" of an antibody include (i) an Fab fragment, a monovalent fragment consisting of the VL, VH, CL and CH1 domains; (ii) an $F(ab')_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al. (1989) *Nature* 341:544-46), which consists of a VH domain; and (vi) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain Fv (scFv); see, e.g., Bird et al. (1988) *Science* 242:423-26; and Huston et al. (1988) *Proc. Natl. Acad. Sci. USA* 85:5879-83). Such single chain antibodies are also intended to be encompassed within the term "antigen binding fragment" of an antibody. These antibody fragments are obtained using conventional techniques known to those skilled in the art, and the fragments are screened for utility in the same manner as are intact antibodies.

Antibody molecules to the polypeptides of the present invention, e.g., antibodies to IL-17F or IL-17R, may be produced by methods well known to those skilled in the art. For example, monoclonal antibodies may be produced by generation of hybridomas in accordance with known methods. Hybridomas formed in this manner are then screened using standard methods, such as an enzyme-linked immunosorbent assay (ELISA), to identify one or more hybridomas that produce an antibody that specifically binds with the polypeptides of the present invention. For example, IL-17F proteins of the invention may be used to immunize animals to obtain polyclonal and monoclonal antibodies that react with the IL-17F protein. Similarly, IL-17R proteins may be used to obtain polyclonal and monoclonal antibodies that specifically react with IL-17R. The peptide immunogens additionally may contain a cysteine residue at the carboxyl terminus, and may be conjugated to a hapten such as keyhole limpet hemocyanin (KLH). Additional peptide immunogens may be generated by replacing tyrosine residues with sulfated tyrosine residues. Methods for synthesizing such peptides are well known in the art, for example, as in Merrifield (1963) *J. Amer. Chem. Soc.* 85:2149-54; Krstenansky et al. (1987) *FEBS Lett.* 211:10. A full-length polypeptide of the present invention may be used as the immunogen, or, alternatively, antigenic peptide fragments of the polypeptides may be used. An antigenic peptide of a polypeptide of the present invention comprises at least 7 continuous amino acid residues and encompasses an epitope such that an antibody raised against the peptide forms a specific immune complex with the polypeptide. Preferably, the antigenic peptide comprises at least 10 amino acid residues, more preferably at least 15 amino acid residues, even more preferably at least 20 amino acid residues, and most preferably at least 30 amino acid residues.

Monoclonal antibodies may be generated by other methods known to those skilled in the art of recombinant DNA technology. As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide related to the present invention (e.g., IL-17F or IL-17R) to thereby isolate immunoglobulin library members that bind to the polypeptides related to the present invention. Techniques and commercially available kits for generating and screening phage display libraries are well known to those skilled in the art. In addition, examples of methods and reagents particularly amenable for use in generating and screening antibody display libraries can be found in the literature. For example, the "combinatorial antibody display" method is well known and was developed to identify and isolate antibody fragments having a particular antigen specificity, and can be utilized to produce monoclonal antibodies (for descriptions of combinatorial antibody display, see, e.g., Sastry et al. (1989) *Proc. Natl. Acad. Sci. USA* 86:5728; Huse et al. (1989) *Science* 246:1275; Orlandi et al. (1989) *Proc. Natl. Acad. Sci. USA* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers to a conserved 3' constant region, can be used for PCR amplification of the heavy and light chain variable regions from a number of murine antibodies (Larrick et al. (1991) *Biotechniques* 11: 152-56). A similar strategy can also been used to amplify human heavy and light chain variable regions from human antibodies (Larrick et al. (1991) *Methods: Companion to Methods in Enzymology* 2:106-10).

Polyclonal sera and antibodies may be produced by immunizing a suitable subject with a polypeptide of the present invention. The antibody titer in the immunized subject may be monitored over time by standard techniques, such as with ELISA using immobilized protein. If desired, the antibody molecules directed against a polypeptide of the present invention may be isolated from the subject or culture media and further purified by well-known techniques, such as protein A chromatography, to obtain an IgG fraction.

Fragments of antibodies to the polypeptides of the present invention may be produced by cleavage of the antibodies in accordance with methods well known in the art. For example, immunologically active Fab and F(ab')$_2$ fragments may be generated by treating the antibodies with an enzyme such as pepsin.

Human antibodies may additionally be produced using transgenic nonhuman animals that are modified so as to produce fully human antibodies rather than the animal's endogenous antibodies in response to challenge by an antigen (see, e.g., PCT publication WO 94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal that provides all the desired modifications is then obtained as progeny by crossbreeding intermediate transgenic animals containing fewer than the full complement of the modifications. The preferred embodiment of such a nonhuman animal is a mouse, and is termed the XENOMOUSE™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

Additionally, chimeric, humanized, and single-chain antibodies to the polypeptides of the present invention, comprising both human and nonhuman portions, may be produced using standard recombinant DNA techniques and/or a recombinant combinatorial immunoglobulin library. Humanized antibodies may also be produced using transgenic mice which are incapable of expressing endogenous immunoglobulin heavy and light chain genes, but which can express human heavy and light chain genes. For example, human monoclonal antibodies (mAbs), e.g., mAb directed against IL-17F, may be generated using transgenic mice carrying the human immunoglobulin genes rather than murine immunoglobulin genes. Splenocytes from these transgenic mice immunized with the antigen of interest may then be used to produce hybridomas that secrete human mAbs with specific affinities for epitopes from a human protein (see, e.g., Wood et al., International Application No. WO 91/00906; Kucherlapati et al., WO 91/10741; Lonberg et al. WO 92/03918; Kay et al., WO 92/03917; Lonberg et al. (1994) Nature 368:856-59; Green et al. (1994) Nat. Genet. 7:13-21; Morrison et al. (1994) Proc. Natl. Acad. Sci. USA 81:6851-55; Bruggeman (1993) Year Immunol 7:33-40; Tuaillon et al. (1993) Proc. Natl. Acad. Sci. USA 90:3720-24; Bruggeman et al. (1991) Eur. J Immunol. 21:1323-26).

Chimeric antibodies, including chimeric immunoglobulin chains, may be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira et al., European Patent Application 184,187; Taniguchi, European Patent Application 171,496; Morrison et al., European Patent Application 173,494; Neuberger et al., WO 86/01533; Cabilly et al., U.S. Pat. No. 4,816,567; Cabilly et al., European Patent Application 125,023; Better et al. (1988) Science 240:1041-43; Liu et al. (1987) Proc. Natl. Acad. Sci. USA 84:3439-43; Liu et al. (1987) J. Immunol. 139:3521-26; Sun et al. (1987) Proc. Natl. Acad. Sci. USA 84:214-18; Nishimura et al. (1987) Cancer Res. 47:999-1005; Wood et al. (1985) Nature 314:446-49; and Shaw et al. (1988) J. Natl. Cancer Inst. 80:1553-59).

An antibody or an immunoglobulin chain may be humanized by methods known in the art. Humanized antibodies, including humanized immunoglobulin chains, may be generated by replacing sequences of the Fv variable region that are not directly involved in antigen binding with equivalent sequences from human Fv variable regions. General methods for generating humanized antibodies are provided by Morrison (1985) Science 229:1202-07; Oi et al. (1986) BioTechniques 4:214; Queen et al., U.S. Pat. Nos. 5,585,089; 5,693,761; 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid sequences are well known to those skilled in the art and, for example, may be obtained from a hybridoma producing an antibody against a predetermined target. The recombinant DNA encoding the humanized antibody, or fragment thereof, then can be cloned into an appropriate expression vector.

Humanized or CDR-grafted antibody molecules or immunoglobulins may be produced by CDR grafting or CDR substitution, wherein one, two, or all CDRs of an immunoglobulin chain can be replaced. See, e.g., U.S. Pat. No. 5,225,539; Jones et al. (1986) Nature 321:552-25; Verhoeyan et al. (1988) Science 239:1534; Beidler et al. (1988) J. Immunol. 141:4053-60; Winter, U.S. Pat. No. 5,225,539, the contents of all of which are hereby incorporated by reference. Winter describes a CDR-grafting method that may be used to prepare the humanized antibodies of the present invention (UK Patent Application GB 2188638A; Winter, U.S. Pat. No. 5,225,539), the contents of which are hereby incorporated by reference. All of the CDRs of a particular human antibody may be replaced with at least a portion of a nonhuman CDR, or only some of the CDRs may be replaced with nonhuman CDRs. It is only necessary to replace the number of CDRs required for binding of the humanized antibody to a predetermined antigen.

Monoclonal, chimeric and humanized antibodies that have been modified by, e.g., deleting, adding, or substituting other portions of the antibody, e.g., the constant region, are also within the scope of the invention. As nonlimiting examples, an antibody can be modified by deleting the constant region, by replacing the constant region with another constant region, e.g., a constant region meant to increase half-life, stability, or affinity of the antibody, or a constant region from another species or antibody class, and by modifying one or more amino acids in the constant region to alter, for example, the number of glycosylation sites, effector cell function, Fc receptor (FcR) binding, complement fixation, etc. Methods for altering an antibody constant region are known in the art. Antibodies with altered function, e.g. altered affinity for an effector ligand, such as FcR on a cell, or the C1 component of complement, can be produced by replacing at least one amino acid residue in the constant portion of the antibody with a different residue (see, e.g., EP 388,151 A1, U.S. Pat. Nos. 5,624,821 and 5,648,260, the contents of all of which are hereby incorporated by reference). Similar types of alterations to the murine (or other species') immunoglobulin may be applied to reduce or eliminate these functions. Such alterations are known in the art. For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or an aromatic nonpolar residue such as phenylalanine, tyrosine, tryptophan or alanine (see, e.g., U.S. Pat. No. 5,624,821). Anti-IL-17F or anti-IL-17R antibodies of the invention may be useful for isolating, purifying, and/or detecting IL-17F or IL-17R polypeptides, respectively, in supernatant, cellular lysate, or on the cell surface. Additionally, a skilled artisan will recognize methods by which antibodies to IL-17F or IL-17R may be used in the screening methods described below. Antibodies disclosed in this invention may be also used diagnostically to monitor, e.g., IL-17F protein levels, as part of a clinical testing procedure, or clinically to target a therapeutic modulator to a cell or tissue comprising the antigen of the antibody. For example, a therapeutic such as a small molecule, or other therapeutic of the invention may be linked to an anti-IL-17F or anti-IL-17R antibody in order to target the therapeutic to the cell or tissue expressing IL-17F or IL-17R, respectively. Alternatively, an antibody to IL-17F or IL-17R may be used as an inhibitory antibody, i.e., an antagonist, to decrease, limit, block, or otherwise reduce IL-17F binding to IL-17R.

In addition to antibodies for use in the instant invention, other molecules may also be employed to modulate the activity of IL-17F homodimers, IL-17A homodimers, and/or IL-17F/IL-17A homodimers. Such molecules include small modular immunopharmaceutical (SMIP™) drugs (Trubion Pharmaceuticals, Seattle, Wash.). SMIPs are single-chain polypeptides composed of a binding domain for a cognate structure such as an antigen, a counterreceptor or the like, a hinge-region polypeptide having either one or no cysteine residues, and immunoglobulin CH2 and CH3 domains (see also www.trubion.com). SMIPs and their uses and applications are disclosed in, e.g., U.S. Published Patent Appln. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

Screening Assays

The related polynucleotides and polypeptides of the invention, including antibodies thereto, may be used in screening assays to identify pharmacological agents or lead compounds for agents, including antibodies, that are capable of modulating the activity of IL-17F in a cell or organism and are thereby potential regulators of inflammatory responses. For example, samples containing IL-17F (either natural or recombinant) may be contacted with one of a plurality of test compounds (either biological agents or small organic molecules), and the biological activity of IL-17F in each of the treated samples can be compared with the biological activity of IL-17F in untreated samples or in samples contacted with different test compounds. Such comparisons will determine whether any of the test compounds results in: 1) a substantially decreased level of expression or biological activity of IL-17F, thereby indicating an antagonist of IL-17F, or 2) a substantially increased level of expression or biological activity of IL-17F, thereby indicating an agonist of IL-17F. In one embodiment, the identification of test compounds capable of modulating IL-17F activity is performed using high-throughput screening assays, such as BIACORE® (Biacore International AB, Uppsala, Sweden), BRET (bioluminescence resonance energy transfer), and FRET (fluorescence resonance energy transfer) assays, as well as ELISA and cell-based assays.

Small Molecules

Decreased IL-17F activity in an organism (or subject) afflicted with (or at risk for) disorders related to IL-17F, e.g., airway inflammation, e.g., in patients with cystic fibrosis, including pulmonary exacerbations due to bacterial infections in same, etc., or in a cell from such an organism (or subject) involved in such disorders, may also be achieved through the use of small molecules (usually organic small molecules) that antagonize, i.e., inhibit the activity of, IL-17F. Novel antagonistic small molecules may be identified by the screening methods described above and may be used in the treatment methods of the present invention described below.

The term small molecule refers to compounds that are not macromolecules (see, e.g., Karp (2000) *Bioinformatics Ontology* 16:269-85; Verkman (2004) *AJP-Cell Physiol*. 286: 465-74). Thus, small molecules are often considered those compounds that are, e.g., less than one thousand daltons (e.g., Voet and Voet, *Biochemistry*, $2^{nd}$ ed., ed. N. Rose, Wiley and Sons, New York, 14 (1995)). For example, Davis et al. (2005) *Proc. Natl. Acad. Sci. USA* 102:5981-86, use the phrase small molecule to indicate folates, methotrexate, and neuropeptides, while Halpin and Harbury (2004) *PLos Biology* 2:1022-30, use the phrase to indicate small molecule gene products, e.g., DNAs, RNAs and peptides. Examples of natural small molecules include, but are not limited to, cholesterols, neurotransmitters, aptamers and siRNAs; synthesized small molecules include, but are not limited to, various chemicals listed in numerous commercially available small molecule databases, e.g., FCD (Fine Chemicals Database), SMID (Small Molecule Interaction Database), ChEBI (Chemical Entities of Biological Interest), and CSD (Cambridge Structural Database) (see, e.g., Alfarano et al. (2005) *Nuc. Acids Res. Database Issue* 33:D416-24).

Methods for Diagnosing, Prognosing, and Monitoring the Progress of Disorders Related to IL-17F The present invention provides methods for diagnosing, prognosing, and monitoring the progress of disorders related to IL-17F in a subject (e.g., disorders that directly or indirectly involve increases in the bioactivity of IL-17F) by detecting an upregulation of IL-17F activity, e.g., by detecting the upregulation of IL-17F, including but not limited to the use of such methods in human subjects. These methods may be performed by, e.g., utilizing prepackaged diagnostic kits comprising at least one of the group comprising an IL-17F or IL-17R polynucleotide (or fragments thereof); an IL-17F or IL-17R polypeptide (or fragments and/or fusion proteins thereof); an antibody to an IL-17F or IL-17R polypeptide (or derivatives thereof); or modulators of IL-17F or IL-17R polynucleotides and/or polypeptides as described herein, which may be conveniently used, for example, in a clinical setting. In addition, one of skill in the art would recognize that the upregulation of, e.g., IL-17F, could also be detected by indirect methods, such as counting the number of immune cells, e.g., neutrophils.

"Diagnostic" or "diagnosing" means identifying the presence or absence of a pathologic condition. Diagnostic methods include detecting upregulation of IL-17F bioactivity by determining a test amount of the gene products (e.g., RNA, cDNA, or polypeptide, including fragments thereof) of IL-17F in a biological sample from a subject (human or nonhuman mammal), and comparing the test amount with a normal amount or range (i.e., an amount or range from an individual(s) known not to suffer from disorders related to IL-17F). Although a particular diagnostic method may not provide a definitive diagnosis of disorders related to IL-17F, it suffices if the method provides a positive indication that aids in diagnosis.

The present invention also provides methods for prognosing such disorders by detecting, for example, the upregulation of IL-17F activity, e.g., by detecting upregulation of IL-17F. "Prognostic" or "prognosing" means predicting the probable development and/or severity of a pathologic condition. Prognostic methods include determining the test amount of a gene product of IL-17F in a biological sample from a subject, and comparing the test amount to a prognostic amount or range (i.e., an amount or range from individuals with varying severities of disorders related to IL-17F) for the gene product of IL-17F. Various amounts of the IL-17F gene product in a test sample are consistent with certain prognoses for disorders related to IL-17F. The detection of an amount of IL-17F gene product at a particular prognostic level provides a prognosis for the subject.

The present invention also provides methods for monitoring the progress or course of such disorders related to IL-17F by detecting, for example, the upregulation of IL-17F activity, e.g., by detecting upregulation of IL-17F. Monitoring methods include determining the test amounts of a gene product of IL-17F in biological samples taken from a subject at a first and second time, and comparing the amounts. A change in amount of an IL-17F gene product between the first and second times indicates a change in the course of an IL-17F-related disorder, with a decrease in amount indicating remission of such disorders, and an increase in amount indicating progression of such disorders. Such monitoring assays are also useful for evaluating the efficacy of a particular therapeutic intervention in patients being treated for autoimmune disorders.

Increased IL-17F in methods outlined above may be detected in a variety of biological samples, including bodily fluids (e.g., whole blood, plasma, and urine), cells (e.g., whole cells, cell fractions, and cell extracts), and other tissues. Biological samples also include sections of tissue, such as biopsies and frozen sections taken for histological purposes. Preferred biological samples include blood, plasma, lymph, tissue biopsies, urine, CSF (cerebrospinal fluid), synovial fluid, and BAL (bronchoalveolar lavage). It will be appreciated that analysis of a biological sample need not necessarily require removal of cells or tissue from the subject. For example, appropriately labeled agents that bind IL-17F gene products (e.g., antibodies, nucleic acids) may be administered to a subject and visualized (when bound to the target) using standard imaging technology (e.g., CAT, NMR (MRI), and PET).

In the diagnostic and prognostic assays of the present invention, the IL-17F gene product is detected and quantified to yield a test amount. The test amount is then compared with a normal amount or range. An amount significantly above the normal amount or range is a positive sign in the diagnosis of disorders related to IL-17F. Particular methods of detection and quantitation of IL-17F gene products are described below.

Normal amounts or baseline levels of IL-17F gene products may be determined for any particular sample type and population. Generally, baseline (normal) levels of IL-17F protein or mRNA are determined by measuring respective amounts of IL-17F protein or mRNA in a biological sample type from normal (i.e., healthy) subjects. Alternatively, normal values of IL-17F gene products may be determined by measuring the amount in healthy cells or tissues taken from the same subject from which the diseased (or possibly diseased) test cells or tissues were taken. The amount of IL-17F gene products (either the normal amount or the test amount) may be determined or expressed on a per cell, per total protein, or per volume basis. To determine the cell amount of a sample, one can measure the level of a constitutively expressed gene product or other gene product expressed at known levels in cells of the type from which the biological sample was taken.

It will be appreciated that the assay methods of the present invention do not necessarily require measurement of absolute values of IL-17F gene products because relative values are sufficient for many applications of these methods. It will also be appreciated that in addition to the quantity or abundance of IL-17F gene products, variant or abnormal IL-17F gene products or their expression patterns (e.g., mutated transcripts, truncated polypeptides) may be identified by comparison to normal gene products and expression patterns.

Whether the expression of a particular gene or protein in two samples is significantly similar or significantly different, e.g., significantly above or significantly below a given level, depends on the gene itself and, inter alia, its variability in expression between different individuals or different samples. It is within the skill in the art to determine whether expression levels are significantly similar or different. Factors such as genetic variation, e.g., in IL-17F and/or IL-17R expression levels, between individuals, species, organs, tissues, or cells may be taken into consideration (when and where necessary) for determining whether the level of expression, e.g., of IL-17F and/or IL-17R, between two samples is significantly similar or significantly different, e.g., significantly above a given level. As a result of the natural heterogeneity in gene expression between individuals, species, organs, tissues, or cells, phrases such as "significantly similar" or "significantly above" cannot be defined as a precise percentage or value, but rather can be ascertained by one skilled in the art upon practicing the invention.

The diagnostic, prognostic, and monitoring assays of the present invention involve detecting and quantifying IL-17F gene products in biological samples. IL-17F gene products include mRNAs and polypeptides, and both can be measured using methods well known to those skilled in the art.

For example, mRNA can be directly detected and quantified using hybridization-based assays, such as Northern hybridization, in situ hybridization, dot and slot blots, and oligonucleotide arrays. Hybridization-based assays refer to assays in which a probe nucleic acid is hybridized to a target nucleic acid. In some formats, the target, the probe, or both are immobilized. The immobilized nucleic acid may be DNA, RNA, or another oligonucleotide or polynucleotide, and may comprise naturally or nonnaturally occurring nucleotides, nucleotide analogs, or backbones. Methods of selecting nucleic acid probe sequences for use in the present invention (based on the nucleic acid sequence of IL-17F) are well known in the art.

Alternatively, mRNA may be amplified before detection and quantitation. Such amplification-based assays are well known in the art and include polymerase chain reaction (PCR), reverse-transcription-PCR (RT-PCR), PCR-enzyme-linked immunosorbent assay (PCR-ELISA), and ligase chain reaction (LCR). Primers and probes for producing and detecting amplified IL-17F gene products (e.g., mRNA or cDNA) may be readily designed and produced without undue experimentation by those of skill in the art based on the nucleic acid sequences of IL-17F. Amplified IL-17F gene products may be directly analyzed, for example, by gel electrophoresis; by hybridization to a probe nucleic acid; by sequencing; by detection of a fluorescent, phosphorescent, or radioactive signal; or by any of a variety of well-known methods. In addition, methods are known to those of skill in the art for increasing the signal produced by amplification of target nucleic acid sequences. One of skill in the art will recognize that, whichever amplification method is used, a variety of quantitative methods known in the art (e.g., quantitative PCR) may be used if quantitation of gene products is desired.

An IL-17F polypeptide (or fragments thereof) may be detected using various well-known immunological assays employing the respective anti-IL-17F antibodies that may be generated as described above. Immunological assays refer to assays that utilize an antibody (e.g., polyclonal, monoclonal, chimeric, humanized, scFv, and/or fragments thereof) that specifically binds to, e.g., an IL-17F polypeptide (or a fragment thereof). Such well-known immunological assays suitable for the practice of the present invention include ELISA, radioimmunoassay (RIA), immunoprecipitation, immunofluorescence, fluorescence-activated cell sorting (FACS), and Western blotting. The ordinarily skilled artisan will also recognize that an IL-17F polypeptide may also be detected using a labeled IL-17R polypeptide(s).

One of skill in the art will understand that the aforementioned methods may be applied to disorders related to IL-17F, including, but not limited to, airway inflammation, e.g., in patients with cystic fibrosis, including pulmonary exacerbations due to bacterial infections in same, etc.

Use of IL-17F Antagonists in Therapy

The inventors believe they are the first to recognize that binding of IL-17R by IL-17F is correlated with airway inflammation, e.g., in patients with cystic fibrosis, including pulmonary exacerbations due to bacterial infections in same. As such, the present invention discloses methods for using IL-17F antagonists to treat airway inflammation, e.g., in patients with cystic fibrosis, including pulmonary exacerbations due to bacterial infections in same.

The IL-17F antagonists disclosed herein, including modulators of IL-17F or IL-17R polynucleotide and/or polypeptide activity identified using the methods described above, may be used in vitro, ex vivo, or incorporated into pharmaceutical compositions and administered to individuals in vivo to treat, for example, airway inflammation, e.g., in patients with cystic fibrosis, including pulmonary exacerbations due to bacterial infections in same, by administration of an IL-17F antagonist (e.g., IL-17F and/or IL-17R inhibitory polynucleotides; soluble IL-17R polypeptides (including fragments and/or fusion proteins thereof); inhibitory anti-IL-17F or anti-IL-17R antibodies; and/or antagonistic small molecules, etc.). Several pharmacogenomic approaches to be considered in determining whether to administer IL-7F antagonists are well known to one of skill in the art and include genome-wide association, candidate gene approach, and gene expression profiling. A pharmaceutical composition of the invention is formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

IL-17F antagonists may be used as pharmaceutical compositions when combined with a pharmaceutically acceptable carrier. Such a composition may contain, in addition to IL-17F antagonists and a carrier, various diluents, fillers, salts, buffers, stabilizers, solubilizers, and other materials well known in the art. The term "pharmaceutically acceptable" means a nontoxic quantity of material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-14, IL-15, G-CSF, stem cell factor, and erythropoietin. The pharmaceutical composition may also include anticytokine antibodies as described in more detail below. The pharmaceutical composition may contain thrombolytic or antithrombotic factors such as plasminogen activator and Factor VIII. The pharmaceutical composition may further contain other anti-inflammatory agents as described in more detail below. Such additional factors and/or agents may be included in the pharmaceutical composition to produce a synergistic effect with IL-17F antagonists, or to minimize side effects caused by the IL-17F antagonist. Conversely IL-17F antagonists may be included in formulations of the particular cytokine, lymphokine, other hematopoietic factor, thrombolytic or antithrombotic factor, or anti-inflammatory agent to minimize side effects of the cytokine, lymphokine, other hematopoietic factor, thrombolytic or antithrombotic factor, or anti-inflammatory agent.

The pharmaceutical composition of the invention may be in the form of a liposome in which IL-17F antagonists are combined, in addition to other pharmaceutically acceptable carriers, with amphipathic agents such as lipids that exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, etc. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are hereby incorporated by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. In practicing the method of treatment or use of the present invention, a therapeutically effective amount of an IL-17F antagonist is administered to a subject, e.g., a mammal (preferably a human). An IL-17F antagonist may be administered in accordance with the method of the invention either alone or in combination with other therapies, such as treatments employing cytokines, lymphokines or other hematopoietic factors, or anti-inflammatory agents. When coadministered with one or more agents, IL-17F antagonists may be administered either simultaneously with the second agent, or sequentially. If administered sequentially, the attending physician will decide on the appropriate sequence of administering, e.g., an IL-17R polypeptide (or fusion protein thereof) and/or inhibitory antibody, in combination with other agents.

When a therapeutically effective amount of an IL-17F antagonist is administered orally, the binding agent will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil (albeit keeping in mind the frequency of peanut allergies in the population), mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition contains from about 0.5 to 90% by weight of the binding agent, and preferably from about 1 to 50% by weight of the binding agent.

When a therapeutically effective amount of an IL-17F antagonist is administered by intravenous, cutaneous or subcutaneous injection, the IL-17F antagonist will be in the form of a pyrogen-free, parenterally acceptable aqueous solution. The preparation of such parenterally acceptable protein solutions, having due regard to pH, isotonicity, stability, and the like, is within the skill of those in the art. A preferred pharmaceutical composition for intravenous, cutaneous, or subcutaneous injection should contain, in addition to the IL-17F antagonist, an isotonic vehicle such as sodium chloride injection, Ringer's injection, dextrose injection, dextrose and sodium chloride injection, lactated Ringer's injection, or other vehicle as known in the art. The pharmaceutical composition of the present invention may also contain stabilizers, preservatives, buffers, antioxidants, or other additive known to those of skill in the art.

The amount of an IL-17F antagonist in the pharmaceutical composition of the present invention will depend upon the nature and severity of the condition being treated, and on the nature of prior treatments that the patient has undergone. Ultimately, the attending physician will decide the amount of an IL-17F antagonist with which to treat each individual patient. Initially, the attending physician will administer low doses of an IL-17F antagonist and observe the patient's response. Larger doses of an IL-17F antagonist may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of IL-17F antagonist, e.g., recombinant IL-17R (including fusion proteins thereof), per kg body weight.

The duration of intravenous (i.v.) therapy using a pharmaceutical composition of the present invention will vary, depending on the severity of the disease being treated and the condition and potential idiosyncratic response of each individual patient. It is contemplated that the duration of each application of an IL-17F antagonist may be in the range of 12 to 24 hours of continuous i.v. administration. Also contemplated is subcutaneous (s.c.) therapy using a pharmaceutical composition of the present invention. These therapies can be administered daily, weekly, or, more preferably, biweekly, or monthly. It is also contemplated that where the IL-17F antagonist is a small molecule (e.g., for oral delivery), the therapies may be administered daily, twice a day, three times a day, etc. Ultimately the attending physician will decide on the appropriate duration of i.v. or s.c. therapy, or therapy with a small molecule, and the timing of administration of the therapy using the pharmaceutical composition of the present invention.

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Use of IL-17F Antagonists to Decrease Airway Inflammation

In one aspect, the invention features a method of decreasing airway inflammation, e.g., in patients with cystic fibrosis, including pulmonary exacerbations due to bacterial infections in same. The method may comprise contacting a population of cells with an IL-17F antagonist (e.g., IL-17F and/or IL-17R inhibitory polynucleotides; soluble IL-17R polypeptides (including fragments and/or fusion proteins thereof); inhibitory anti-IL-17F or anti-IL-17R antibodies; and/or antagonistic small molecules, etc.) in an amount sufficient to inhibit the IL-17F activity of the cell or population.

These methods are based, at least in part, on the finding that IL-17F binds to IL-17R (Example 4) and that IL-17F concentration in sputum of patients with cystic fibrosis is directly correlated with the degree of pulmonary exacerbation (Example 8). Accordingly, IL-17F antagonists, i.e., molecules that inhibit IL-17F activity (e.g., anti-IL-17F antibodies), may be used to decrease airway inflammation, e.g., in patients with cystic fibrosis, including pulmonary exacerbations due to bacterial infections in same.

The methods of using IL-17F antagonists may also be used inhibit IL-17F inflammatory activity and thus, can be used to treat or prevent a variety of immune disorders. Nonlimiting examples of the disorders that can be treated or prevented include, but are not limited to, transplant rejection, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosus, autoimmune thyroiditis, dermatitis (including atopic dermatitis and eczematous dermatitis), psoriasis, Sjögren's syndrome, Crohn's disease, aphthous ulcer, iritis, conjunctivitis, keratoconjunctivitis, ulcerative colitis, spondyloarthropathy, ankylosing spondylitis, intrinsic asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, and allergy such as, atopic allergy. Preferred disorders that can be treated using methods, which comprise the administration of IL-17F antagonists, e.g., an inhibitory IL-17F antibody, include airway inflammation, e.g., in patients with cystic fibrosis, including pulmonary exacerbations due to bacterial infections in same.

Using IL-17F antagonists (e.g., IL-17F and/or IL-17R inhibitory polynucleotides; soluble IL-17R polypeptides (including fragments and/or fusion proteins thereof); inhibitory anti-IL-17F or anti-IL-17R antibodies; and/or antagonistic small molecules, etc.), it is possible to modulate immune responses in a number of ways. Downregulation may be in the form of inhibiting or blocking an inflammatory response already in progress, or may involve preventing the induction of an inflammatory response.

In one embodiment, IL-17F antagonists, including pharmaceutical compositions thereof, are administered in combination therapy, i.e., combined with other agents, e.g., therapeutic agents, that are useful for treating pathological conditions or disorders, such as immune disorders and inflammatory diseases (including airway inflammation). The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more IL-17F antagonists (e.g., IL-17F and/or IL-17R inhibitory polynucleotides; soluble IL-17R polypeptides (including fragments and/or fusion proteins thereof); inhibitory anti-IL-17F or anti-IL-17R antibodies; and/or antagonistic small molecules, etc.) coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more IL-17F antagonists described herein may be used in combination with two or more of the therapeutic agents described herein. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-17F signaling pathway, and thus are expected to enhance and/or synergize with the effects of the IL-17F antagonists.

Preferred therapeutic agents used in combination with an IL-17F antagonist are those agents that interfere at different stages in an inflammatory response (including airway inflammation). In one embodiment, one or more IL-17F antagonists described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof. Thus, one or more IL-17F antagonists described herein may be used in combination with one or more cytokine inhibitors, growth factor inhibitors, immunosuppressants, anti-inflammatory agents, metabolic inhibitors, enzyme inhibitors, cytotoxic agents, and cytostatic agents. Nonlimiting examples of the agents that can be used in combination with the IL-17F antagonists described herein, include, but are not limited to, antagonists of one or more interleukins (ILs) or their receptors, e.g., antagonists of IL-1, IL-2, IL-6, IL-7, IL-8, IL-12, IL-13, IL-15, IL-16, IL-18, and IL-22; antagonists of cytokines or growth factors or their receptors, such as tumor necrosis factor (TNF), LT, EMAP-II, GM-CSF, FGF and PDGF. IL-17F antagonists can also be combined with inhibitors of, e.g., antibodies to, cell surface molecules such as CD2, CD3, CD4, CD8, CD20 (e.g., the CD20 inhibitor rituximab (RITUXAN®)), CD25, CD28, CD30, CD40, CD45, CD69, CD80 (B7.1), CD86 (B7.2), CD90, or their ligands, including CD154 (gp39 or CD40L), or LFA-1/ICAM-1 and VLA-4/VCAM-1 (Yusuf-Makagiansar et al. (2002) Med. Res. Rev. 22:146-67). Preferred antagonists that can be used in combination with IL-17F antagonists described herein include antagonists of IL-1, IL-12, TNFα, IL-15, IL-18, and IL-22.

Examples of those agents include IL-12 antagonists, such as chimeric, humanized, human or in vitro-generated antibodies (or antigen binding fragments thereof) that bind to IL-12 (preferably human IL-12), e.g., the antibody disclosed in WO 00/56772; IL-12 receptor inhibitors, e.g., antibodies to human IL-12 receptor; and soluble fragments of the IL-12 receptor, e.g., human IL-12 receptor. Examples of IL-15 antagonists include antibodies (or antigen binding fragments thereof) against IL-15 or its receptor, e.g., chimeric, humanized, human or in vitro-generated antibodies to human IL-15 or its receptor, soluble fragments of the IL-15 receptor, and IL-15-binding proteins. Examples of IL-18 antagonists include antibodies, e.g., chimeric, humanized, human or in vitro-generated antibodies (or antigen binding fragments thereof), to human IL-18, soluble fragments of the IL-18 receptor, and IL-18 binding proteins (IL-18BP, Mallat et al. (2001) Circ. Res. 89:e41-45). Examples of IL-1 antagonists include interleukin-1-converting enzyme (ICE) inhibitors, such as Vx740, IL-1 antagonists, e.g., IL-1RA (anakinra-KINERET™, Amgen), sIL1RII (Immunex), and anti-IL-1 receptor antibodies (or antigen binding fragments thereof).

Examples of TNF antagonists include chimeric, humanized, human or in vitro-generated antibodies (or antigen binding fragments thereof) to TNF (e.g., human TNFα), such as HUMIRA™ (D2E7, human TNFα antibody, U.S. Pat. No. 6,258,562), CDP-571/CDP-870/BAY-10-3356 (humanized anti-TNFα antibody; Celltech/Pharmacia), cA2 (chimeric anti-TNFα antibody; REMICADE®, Centocor); anti-TNF antibody fragments (e.g., CPD870); soluble fragments of the TNF receptors, e.g., p55 or p75 human TNF receptors or derivatives thereof, e.g., 75 kd TNFR-IgG (75 kD TNF receptor-IgG fusion protein, ENBREL™; Immunex), p55 kd TNFR-IgG (55 kD TNF receptor-IgG fusion protein (LENERCEPT®); enzyme antagonists, e.g., TNFα converting enzyme (TACE) inhibitors (e.g., an alpha-sulfonyl hydroxamic acid derivative, WO 01/55112, and N-hydroxyformamide TACE inhibitor GW 3333, –005, or –022); and TNF-bp/s-TNFR (soluble TNF binding protein). Preferred TNF antagonists are soluble fragments of the TNF receptors, e.g., p55 or p75 human TNF receptors or derivatives thereof, e.g., 75 kdTNFR-IgG, and TNFα converting enzyme (TACE) inhibitors.

In other embodiments, the IL-17F antagonists described herein may be administered in combination with one or more of the following: IL-13 antagonists, e.g., soluble IL-13 receptors (sIL-13) and/or antibodies against IL-13; IL-2 antagonists, e.g., DAB 486-IL-2 and/or DAB 389-IL-2 (IL-2 fusion proteins), and/or antibodies to IL-2R, e.g., anti-Tac (humanized anti-IL-2R; Protein Design Labs). Yet another combination includes IL-17F antagonists (e.g., IL-17F and/or IL-17R inhibitory polynucleotides; soluble IL-17R polypeptides (including fragments and/or fusion proteins thereof); inhibitory anti-IL-17F or anti-IL-17R antibodies; and/or antagonistic small molecules, etc.), in combination with nondepleting anti-CD4 inhibitors (IDEC-CE9.1/SB 210396; nondepleting primatized anti-CD4 antibody; IDEC/SmithKline). Yet other preferred combinations include antagonists of the costimulatory pathway CD80 (B7.1) or CD86 (B7.2), including antibodies, soluble receptors or antagonistic ligands; as well as p-selectin glycoprotein ligand (PSGL), anti-inflammatory cytokines, e.g., IL-4 (DNAX/Schering); IL-10 (SCH 52000;

recombinant IL-10 DNAX/Schering); IL-13 and TGF-β, and agonists thereof (e.g., agonist antibodies).

In other embodiments, one or more IL-17F antagonists can be coformulated with, and/or coadministered with, one or more anti-inflammatory drugs, immunosuppressants, or metabolic or enzymatic inhibitors. Nonlimiting examples of the drugs or inhibitors that can be used in combination with the IL-17F antagonists described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl)methyl]methylamino]benzoyl]-L-glutamic acid); and inhibitors of pyrimidine biosynthesis, e.g., dihydroorotate dehydrogenase (DHODH) inhibitors (e.g., leflunomide). Preferred therapeutic agents for use in combination with IL-17F antagonists include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppresants, e.g., cyclosporin, tacrolimus (FK-506); and mTOR inhibitors, e.g., sirolimus (rapamycin-RAPAMUNE™) or rapamycin derivatives, e.g., soluble rapamycin derivatives (e.g., ester rapamycin derivatives, e.g., CCI-779 (Elit (2002) Curr. Opin. Investig. Drugs 3(8):1249-53; Huang et al. (2002) Curr. Opin. Investig. Drugs 3(2):295-304); agents which interfere with signaling by proinflammatory cytokines such as TNFα or IL-1 (e.g. IRAK, NIK, IKK, p38 or MAP kinase inhibitors); Cox2 inhibitors, e.g., celecoxib, rofecoxib, and variants thereof; phosphodiesterase inhibitors, e.g., R973401 (phosphodiesterase Type IV inhibitor)phospholipase inhibitors, e.g., inhibitors of cytosolic phospholipase 2 (cPLA2) (e.g., trifluoromethyl ketone analogs (U.S. Pat. No. 6,350,892)); inhibitors of vascular endothelial cell growth factor or growth factor receptor, e.g., VEGF inhibitor and/or VEGF-R inhibitor; and inhibitors of angiogenesis. Preferred therapeutic agents for use in combination with IL-17F antagonists are immunosuppresants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); Cox2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with an IL-17F antagonist include one or more of: 6-mercaptopurines (6-MP); azathioprine; sulphasalazine; mesalazine; olsalazine; chloroquinine/hydroxychloroquine (PLAQUENIL®); pencillamine; aurothiomalate (intramuscular and oral); azathioprine; colchicine; beta-2 adrenoreceptor agonists (salbutamol, terbutaline, salmeterol); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

The use of the IL-17F antagonists disclosed herein in combination with other therapeutic agents to treat or prevent specific disorders related to IL-17F is discussed in further detail below.

Nonlimiting examples of agents for treating or preventing arthritic disorders (e.g., rheumatoid arthritis, inflammatory arthritis, rheumatoid arthritis, juvenile rheumatoid arthritis, osteoarthritis and psoriatic arthritis), with which IL-17F antagonists may be combined include one or more of the following: IL-12 antagonists as described herein; NSAIDs; CSAIDs; TNFs, e.g., TNFα, antagonists as described herein; nondepleting anti-CD4 antibodies as described herein; IL-2 antagonists as described herein; anti-inflammatory cytokines, e.g., IL-4, IL-10, IL-13 and TGFα, or agonists thereof; IL-1 or IL-1 receptor antagonists as described herein; phosphodiesterase inhibitors as described herein; Cox-2 inhibitors as described herein; iloprost: methotrexate; thalidomide and thalidomide-related drugs (e.g., Celgen); leflunomide; inhibitor of plasminogen activation, e.g., tranexamic acid; cytokine inhibitor, e.g., T-614; prostaglandin E1; azathioprine; an inhibitor of interleukin-1 converting enzyme (ICE); zap-70 and/or lck inhibitor (inhibitor of the tyrosine kinase zap-70 or lck); an inhibitor of vascular endothelial cell growth factor or vascular endothelial cell growth factor receptor as described herein; an inhibitor of angiogenesis as described herein; corticosteroid anti-inflammatory drugs (e.g., SB203580); TNF-convertase inhibitors; IL-11; IL-13; IL-17 inhibitors; gold; penicillamine; chloroquine; hydroxychloroquine; chlorambucil; cyclophosphamide; cyclosporine; total lymphoid irradiation; antithymocyte globulin; CD5-toxins; orally administered peptides and collagen; lobenzarit disodium; cytokine regulating agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline (MINOCIN®); anti-IL2R antibodies; marine and botanical lipids (fish and plant seed fatty acids); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine. Preferred combinations include one or more IL-17F antagonists (e.g., IL-17F and/or IL-17R inhibitory polynucleotides; soluble IL-17R polypeptides (including fragments and/or fusion proteins thereof); inhibitory anti-IL-17F or anti-IL-17R antibodies; and/or antagonistic small molecules, etc.) in combination with methotrexate or leflunomide, and in moderate or severe rheumatoid arthritis cases, cyclosporine.

Preferred examples of inhibitors to use in combination with IL-17F antagonists to treat arthritic disorders include TNF antagonists (e.g., chimeric, humanized, human or in vitro-generated antibodies, or antigen binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, ENBREL™), p55 kD TNF receptor-IgG fusion protein; TNF enzyme antagonists, e.g., TNFα converting enzyme (TACE) inhibitors); antagonists of IL-12, IL-15, IL-18, IL-22; T cell and B cell-depleting agents (e.g., anti-CD4 or anti-CD22 antibodies); small molecule inhibitors, e.g., methotrexate and leflunomide; sirolimus (rapamycin-RAPAMUNE®) and analogs thereof, e.g., CCI-779; cox-2 and cPLA2 inhibitors; NSAIDs; p38 inhibitors, TPL-2, Mk-2 and NFκB inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFκB antagonists. Most preferred additional therapeutic agents that can be coadministered and/or coformulated with one or more IL-17F antagonists (e.g., IL-17F and/or IL-17R inhibitory polynucleotides; soluble IL-17R polypeptides (including fragments and/or fusion proteins thereof)); inhibitory anti-IL-17F or anti-IL- 17R antibodies; and/or antagonistic small molecules, etc.) include one or more of: a soluble fragment of a TNF receptor, e.g., p55 or p75 human TNF receptor or derivatives thereof, e.g., 75 kdTNFR-IgG (75 kD TNF receptor-IgG fusion protein, ENBREL™); methotrexate, leflunomide, or a sirolimus (rapamycin) or an analog thereof, e.g., CCI-779.

Nonlimiting examples of agents for treating or preventing multiple sclerosis with which IL-17F antagonists can be combined include the following: interferons, e.g., interferon-alphala (e.g., AVONEX™; Biogen) and interferon-1b (BETASERON™ Chiron/Berlex); Copolymer 1 (Cop-1; COPAXONE™ Teva Pharmaceutical Industries, Inc.); hyperbaric oxygen; intravenous immunoglobulin; cladribine; TNF antagonists as described herein; corticosteroids; prednisolone; methylprednisolone; azathioprine; cyclophosphamide; cyclosporine; cyclosporine A, methotrexate; 4-aminopyridine; and tizanidine. Additional antagonists that can be used in combination with IL-17F antagonists include antibodies to or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. IL-17F antagonists as described herein can be combined with antibodies to cell surface molecules such as CD2, CD3, CD4, CD8, CD25, CD28, CD30, CD40, CD45, CD69, CD80, CD86, CD90 or their ligands. The IL-17F antagonists may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines as described herein, IL-Ib converting enzyme inhibitors (e.g., Vx740), anti-P7s, PSGL, TACE inhibitors, T-cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, and anti-inflammatory cytokines (e.g., IL-4, IL-10, IL-13 and TGF).

Preferred examples of therapeutic agents for multiple sclerosis with which the IL-17F antagonists can be combined include interferon-β, for example, IFNβ-1a and IFNβ-1b; copaxone, corticosteroids, IL-I inhibitors, TNF inhibitors, antibodies to CD40 ligand and CD80, IL-12 antagonists.

Nonlimiting examples of agents for treating or preventing inflammatory bowel disease (e.g., Crohn's disease, ulcerative colitis) with which a IL-17F antagonist (e.g., IL-17F and/or IL-17R inhibitory polynucleotides; soluble IL-17R polypeptides (including fragments and/or fusion proteins thereof); inhibitory anti-IL-17F or anti-IL-17R antibodies; and/or antagonistic small molecules, etc.) can be combined include the following: budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of platelet activating factor (PAF); ciprofloxacin; and lignocaine.

In one embodiment, an L-17F antagonist (e.g., IL-17F and/or IL-17R inhibitory polynucleotides; soluble IL-17R polypeptides (including fragments and/or fusion proteins thereof)); inhibitory anti-IL-17F or anti-IL-17R antibodies; and/or antagonistic small molecules, etc.) can be used in combination with one or more antibodies directed at other targets involved in regulating immune responses, e.g., transplant rejection. Nonlimiting examples of agents for treating or preventing immune responses with which an IL-17F antagonist of the invention can be combined include the following: antibodies against other cell surface molecules, including but not limited to CD25 (interleukin-2 receptor-a), CD11a (LFA-1), CD54 (ICAM-1), CD4, CD45, CD28/CTLA4 (CD80 (B7.1), e.g., CTLA4 Ig-abatacept (ORENCIA®), ICOSL, ICOS and/or CD86 (B7.2). In yet another embodiment, an IL-17F antagonist is used in combination with one or more general immunosuppressive agents, such as cyclosporin A or FK506.

In other embodiments, IL-17F antagonists are used as vaccine adjuvants against inflammatory diseases, e.g., airway inflammation, e.g., in patients with cystic fibrosis, including pulmonary exacerbations due to bacterial infections in same. The combination of adjuvants for treatment of these types of disorders are suitable for use in combination with a wide variety of antigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

For example, desirable vaccines for moderating responses to allergens in a vertebrate host, which contain the adjuvant combinations of this invention, include those containing an allergen or fragment thereof. Examples of such allergens are described in U.S. Pat. No. 5,830,877 and published International Patent Application No. WO 99/51259, which are hereby incorporated by reference in their entireties, and include pollen, insect venoms, animal dander, fungal spores and drugs (such as penicillin). The vaccines interfere with the production of IgE antibodies, a known cause of allergic reactions. In another example, desirable vaccines for preventing or treating disease characterized by amyloid deposition in a vertebrate host, which contain the adjuvant combinations of this invention, include those containing portions of amyloid peptide protein (APP). This disease is referred to variously as Alzheimer's disease, amyloidosis or amyloidogenic disease. Thus, the vaccines of this invention include the adjuvant combinations of this invention plus Aβ peptide, as well as fragments of Aβ peptide and antibodies to Aβ peptide or fragments thereof.

Methods of 1) downregulating antigen presenting cell function; and 2) combination therapy for managing immunosuppression are well known in the art (see, e.g., Xiao et al. (2003) *BioDrugs* 17:103-11; Kuwana (2002) *Hum. Immunol.* 63:1156-63; Lu et al. (2002) *Transplantation* 73:S19-S22; Rifle et al. (2002) *Transplantation* 73:S1-S2; Mancini et al. (2004) *Crit. Care. Nurs. Q.* 27:61-64).

Another aspect of the present invention accordingly relates to kits for carrying out the administration of IL-17F antagonists (e.g., IL-17F or IL-17R inhibitory polynucleotides; soluble IL-17R polypeptides (including fragments and/or fusion proteins thereof; inhibitory anti-17F or anti-IL-17R antibodies; and/or antagonistic small molecules, etc.). In one embodiment, the kit comprises one or more binding agents formulated in a pharmaceutical carrier, and at least one agent, e.g., therapeutic agent, formulated as appropriate, in one or more separate pharmaceutical preparations.

The entire contents of all references, patents, and published patent applications cited throughout this application are hereby incorporated by reference herein.

EXAMPLES

The following Examples provide illustrative embodiments of the invention and do not in any way limit the invention. One of ordinary skill in the art will recognize that numerous other embodiments are encompassed within the scope of the invention.

Example 1

Materials and Methods

Example 1.1

Primary Cell Culture from Human Airway Tissues

Human bronchial epithelial (HBE) cells were isolated from native lungs of transplant recipients, or unused sections of the donor lungs as previously described (Devor et al. (2000) *Am. J. Physiol.—Cell Physiol.* 279:C461-79). Airways were dissected from surrounding adventitial tissue, and placed in ice-cold HEPES-buffered minimum essential medium containing penicillin, streptomycin, and amphotericin B. After multiple washes with cold Hanks' balanced salt solution (HBSS), cartilaginous airway segments were cut longitudinally, and incubated overnight at 4° C. in 0.1% Protease XIV (Sigma, St. Louis, Mo.). Airway epithelial cells were obtained by gently scraping the epithelium with the blunt end of forceps. Recovered cells were plated on type IV human placental collagen (Sigma) coated tissue culture plates in 1:1 mixture of bronchial epithelial growth media (BEGM; Clonetics Corp., San Diego, Calif.) and Keratinocyte-Serum Free Media (K-SFM; Invitrogen Corp.). After 5-7 days under these conditions, cells were trypsinized, washed in HBSS and seeded onto type IV human placental collagen coated Corning/CoStar Transwell filters at 100% confluence in BEGM/K-SFM. After 24 h, cells were placed at air-liquid interface by removing apical media from the Transwell filter, and basolateral media was replaced with DMEM/F12 (Invitrogen Corp.) containing 2% UltroSer G (BioSepra) to promote differentiation. Under biphasic culture conditions, a mucociliary epithelium with the formation of cilia and mucus-secreting granules was observed. The cultures were deprived of serum 24 h before initiating cytokine treatment.

Example 1.2

Cytokines and Antibody Treatment

IL-17A and IL-17F (R&D Systems, Minneapolis, Minn.) were dissolved in F12/DMEM and added directly to both the apical and/or basal surfaces of primary HBE cultures at final concentrations of 0, 1, 10 or 100 ng/ml. TNF-α (Biosource International, Camarillo, Calif.) was used at a final concentration of 1 ng/ml. To test the inhibitory effects of a monoclonal anti-human IL-17 receptor antibody (R&D Systems) on IL-17F bioactivity, the antibody was added to the cultures at a final concentration of 2 µg/ml, which is ten-fold greater than the ED50, and cytokine, chemokine and/or growth factor secretion by human dermal fibroblasts was determined. Recombinant human IL-17R:Fc chimera (R&D Systems) was used at 1 µg/ml. In TNF receptor neutralization studies, anti-human TNF-RI (Biosource International) was used at a concentration of 10 µg/ml and/or recombinant human TNF-RII:Fc chimera (R&D Systems) was used at a concentration of 0.5 µg/ml.

Example 1.3

RNA Isolation/RT-PCR Analysis of DEFB4 Gene Expression

RNA was extracted from cultures after 24 h of incubation using TriZOL LS reagent (Invitrogen) according to the manufacturer's protocol. Taqman PCR was carried out to examine Human Beta Defensin-4 (DEFB104) gene expression after reverse transcription and amplification on an ABI PRISM 7700 Sequence Detection System (Applied Biosystems). Gene-specific primers for DEFB104 were purchased from Applied Biosystems. The PCR reaction was carried out in 96-well optical reaction plates and each well contained a 50 µl reaction mixture with 25 µl of SYBR Green PCR Master Mix, 0.5 µl of each primer (final concentration: 900 nM), 19 µl of water and 5 µl of cDNA samples. The threshold cycle (Ct) value reflects the cycle number at which the fluorescence generated within a reaction exceeds two standard deviations. The relative mRNA amount of each sample was calculated based on its Ct in comparison to the Ct of a housekeeping gene, 18s. The results are presented as comparative expression level ($2^{-\Delta\Delta CT}$). Real Time PCR was conducted in triplicate for each sample and the mean value was calculated. This procedure was performed in at least 3 independent experiments.

Example 1.4

Bio-Plex and ELISA Measurements

A Bio-Plex human cytokine assay (BIO-RAD) for simultaneous quantification of IL-1β, IL-2, IL-4, IL-5, IL-6, IL-7, IL-8, IL-10, IL-12p70, IL-13, IL-17, G-CSF, GM-CSF, IFN-γ, MCP-1, MIP-1β, and TNF-α in apical and basolateral media was run according to the recommended procedure. G-CSF and GRO-α were measured using separate ELISA kits (R&D Systems) following manufacturer's instructions. Human IL-17F was measured using antibodies provided by Wyeth (Cambridge, Mass.).

Example 1.5

Immunohistochemistry

Anti-human IL-17R antibody (Santa Cruz Biotechnology, Santa Cruz, Calif.) was used to characterize the expression of IL-17 receptor on respiratory epithelial cells from human lung tissue sections. The staining was carried out using Cy-3 conjugated rabbit anti-goat as secondary antibody (Sigma) and fluoromount G as mounting medium. Rabbit serum was used for blocking prestaining. The staining pictures were captured by a camera attached to an Olympus Provis fluorescent microscope and images were further analyzed with Olympus Software (Olympus, Melville, N.Y.).

To characterize the expression of TNF receptors I (TNF-RI) and II (TNF-RII) on polarized HBE cells grown on air liquid interface, mouse anti-human TNF-RI and TNF-RII monoclonal antibodies (R&D Systems) were used as primary antibodies and Alexa 488 goat antibody (Molecular Probes, Eugene, Oreg.) was used as a secondary antibody. Prolong Gold antifade with DAPI (Molecular Probes) was used as a mounting medium. Images were captured by a camera attached to an Axioplan 2 universal imaging microscope, and further analyzed with Slidebook 4.0 software (both from Intelligent Imaging Innovations, Denver, Colo.) and Metamorph software (Universal Imaging Corp., Downingtown, Pa.).

Example 1.6

Human Subjects

Adult patients with cystic fibrosis (mean age 22) colonized with *P. aeruginosa* undergoing pulmonary exacerbation requiring hospitalization were enrolled in a study to measure biomarkers of inflammation in sputum on day 1 of hospitalization, and 10 and 20 days after initiation of antibiotics and intensified respiratory therapy. Sputum samples were processed using Sputolysin (Behring Diagnostics, Somerville, N.J.). Briefly, 1 ml of 10% Sputolysin was added per 1 mg of sputum, the sample was incubated for 5 min at 37° C. with vigorous shaking and mixed vigorously with transfer pipette. Samples were then centrifuged at 2000 rpm for 5 min at 4° C. and supernatants were assayed by Bio-Plex and ELISA.

Example 1.7

Western Blot Analysis

Western blot samples from processed sputum were separated (12.4 μg of protein per lane) on SDS-PAGE. Proteins separated on gels were transferred onto Immobilon-P membranes (Millipore, Bedford, Mass.) at 140 mA for 1 h. The membranes were blocked overnight at 4° C. with PBS containing 5% BSA. The blots were stained with rabbit anti-human-p19 antibody for 1 h at room temperature and developed by incubation with a secondary alkaline phosphatase-conjugated goat anti-rabbit IgG (Bio-Rad) and BCIP/NBT reagent (Bio-Rad Laboratories, Hercules, Calif.).

Example 1.8

Statistical Analysis

Data were analyzed using StatView statistical software (Brainpower Inc., Calabasas, Calif.). Comparisons between groups where data were normally distributed were made with Student's t-test, and comparisons among multiple groups or nonparametric data were made with analyses of variance. Scheffe's test was used as the post hoc test. The Mann-Whitney test or the Wilcoxon paired sample test was employed to make ordinal comparisons. Significance was accepted at a p value <0.05.

Example 2

Figure 1:
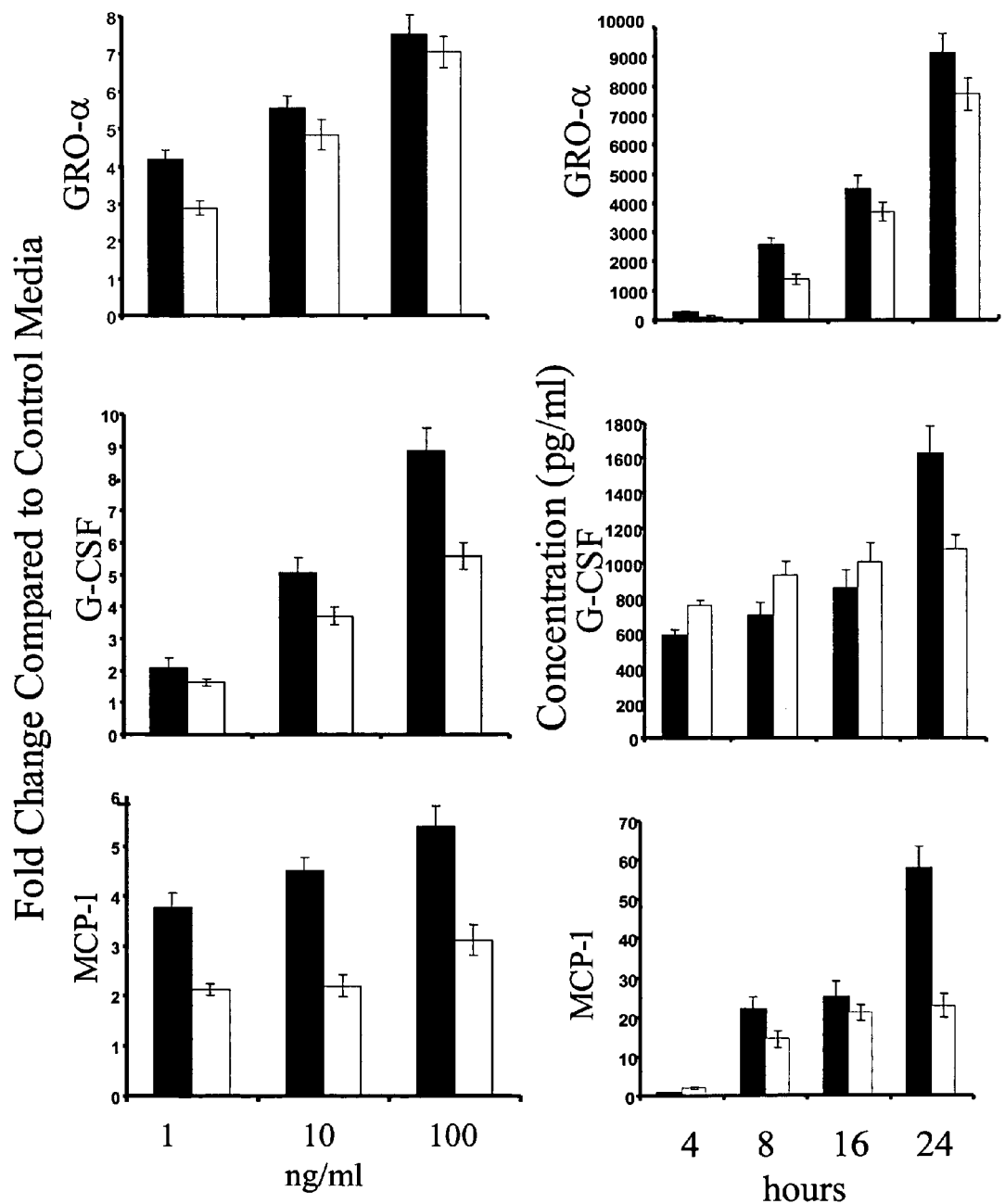

IL-17F Upregulates G-CSF, GRO-α and MCP-1 Expression by Human Bronchial Epithelial Cells Using Bio-Plex and ELISA assays as described in Example 1.1, both apical and basolateral media were screened for cytokines, chemokines and/or growth factors that may be regulated by IL-17A and IL-17F in human primary bronchial epithelial cells grown at the air-liquid interface (see Example 1). In addition to IL-8 and IL-6, two factors already reported to be induced by IL-17A (data not shown), a significant induction in G-CSF, GRO-α and MCP-1 secretion was detected at 24 h in primary HBE cells treated with IL-17A and IL-17F (Table 2). The data are graphed as fold induction because of the variability in the absolute amount of growth factors secreted from different airway donors. These effects were dose-dependent (FIG. 1A; Table 2) with a maximal effect observed at a concentration of 100 ng/ml. IL-17A was more potent than IL-17F on a weight per weight basis to induce G-CSF, GRO-α and MCP-1 at 24 h. A time course performed with 10 ng/ml of IL-17A and IL-17F showed that the effects of IL-17A and IL-17F on G-CSF, GRO-α and MCP-1 were time-dependent (FIG. 1B), with a maximum effect observed at 24 h. Based on these kinetic studies, most of the following experiments were performed using 10 ng/ml of IL-17A or IL-17F and an incubation time of 24 h.

TABLE 2

Concentration of G-CSF, GRO-α and MCP-1 in Basolateral Media after 24 h of HBE Stimulation with IL-17A and IL-17F

|  | G-CSF | GRO-α | MCP-1 |
| --- | --- | --- | --- |
| IL-17A |  |  |  |
| 0 ng/ml | 401.2 ± 32.24 | 2012.1 ± 102.34 | 22.01 ± 1.98 |
| 1 ng/ml | 829.56 ± 128.38 | 8412.1 ± 503.02 | 82.8 ± 6.6 |
| 10 ng/ml | 2029.3 ± 192.57 | 11144.7 ± 643.87 | 98.83 ± 6.16 |
| 100 ng/ml | 3546.24 ± 296.88 | 15140.7 ± 1026.17 | 118.5 ± 8.8 |
| IL-17F |  |  |  |
| 0 ng/ml | 401.2 ± 32.24 | 2012.1 ± 102.34 | 22.01 ± 1.98 |
| 1 ng/ml | 655.4 ± 44.13 | 5798.1 ± 382.30 | 46.75 ± 2.64 |
| 10 ng/ml | 1482 ± 112.33 | 9729.2 ± 804.84 | 43.36 ± 4.13 |
| 100 ng/ml | 2236 ± 164.49 | 14175.4 ± 865.20 | 68.5 ± 6.61 |

Example 3

IL-17F is Synergistic with TNF-α for Induction of G-CSF and GRO-α Secretion

Figure 2:
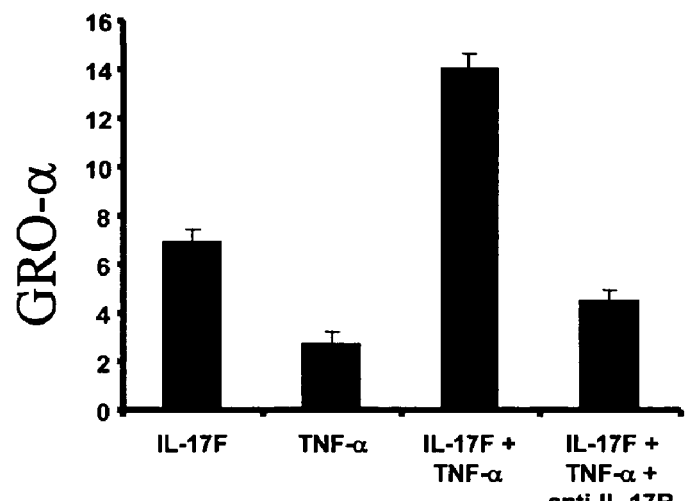
Figure 2:
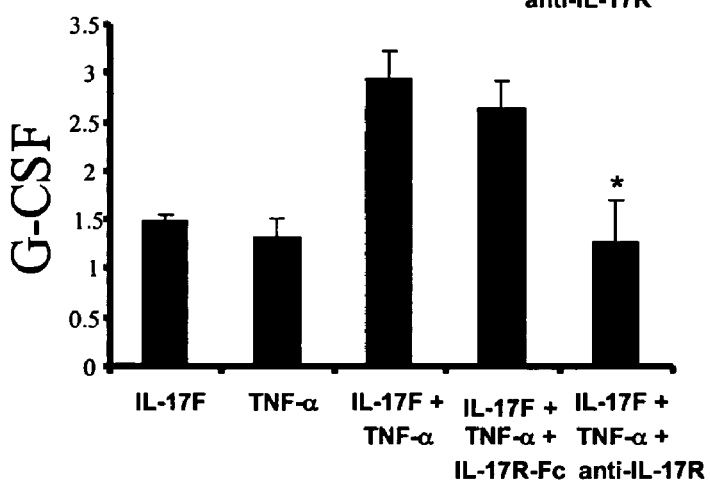
Figure 2:
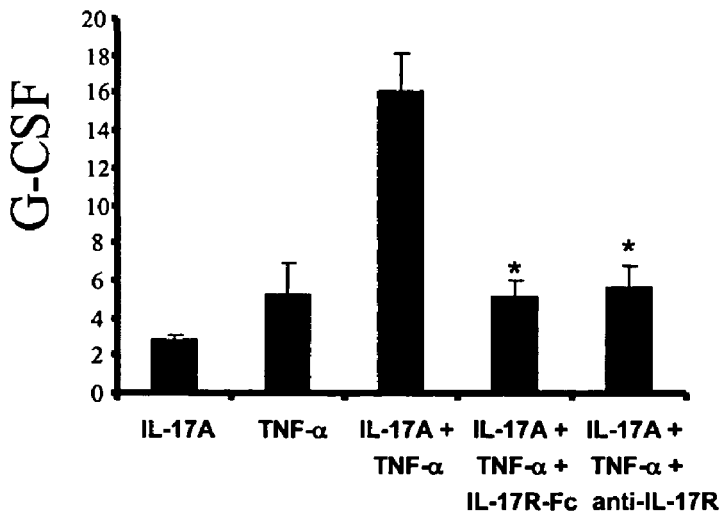

As synergy of IL-17A with TNF-α has been reported, the effect of combining IL-17F (10 ng/ml) and TNF-α (1 ng/ml) to upregulate G-CSF and GRO-α secretion by primary HBE cells was determined. Optimal concentrations of cytokines had been determined in previous experiments (data not shown). HBE cells showed a synergistic effect in G-CSF and GRO-α secretion when IL-17F was combined with TNF-α for 24 h (FIGS. 2A and 2B). This synergistic effect was inhibited by preincubating the stimulating cytokine mixture with an anti-IL-17R mAb, but not with a soluble IL-17R:Fc chimera protein or an isotype matched control Ab (isotype data not shown). However, both anti-IL-17R mAb and soluble IL-17R:Fc proteins were effective in inhibiting IL-17A-induced increases in G-CSF (FIG. 2C). These data strongly suggest that IL-17R is critical for both IL-17A- and IL-17F-induced G-CSF responses.

Example 4

Figure 3:
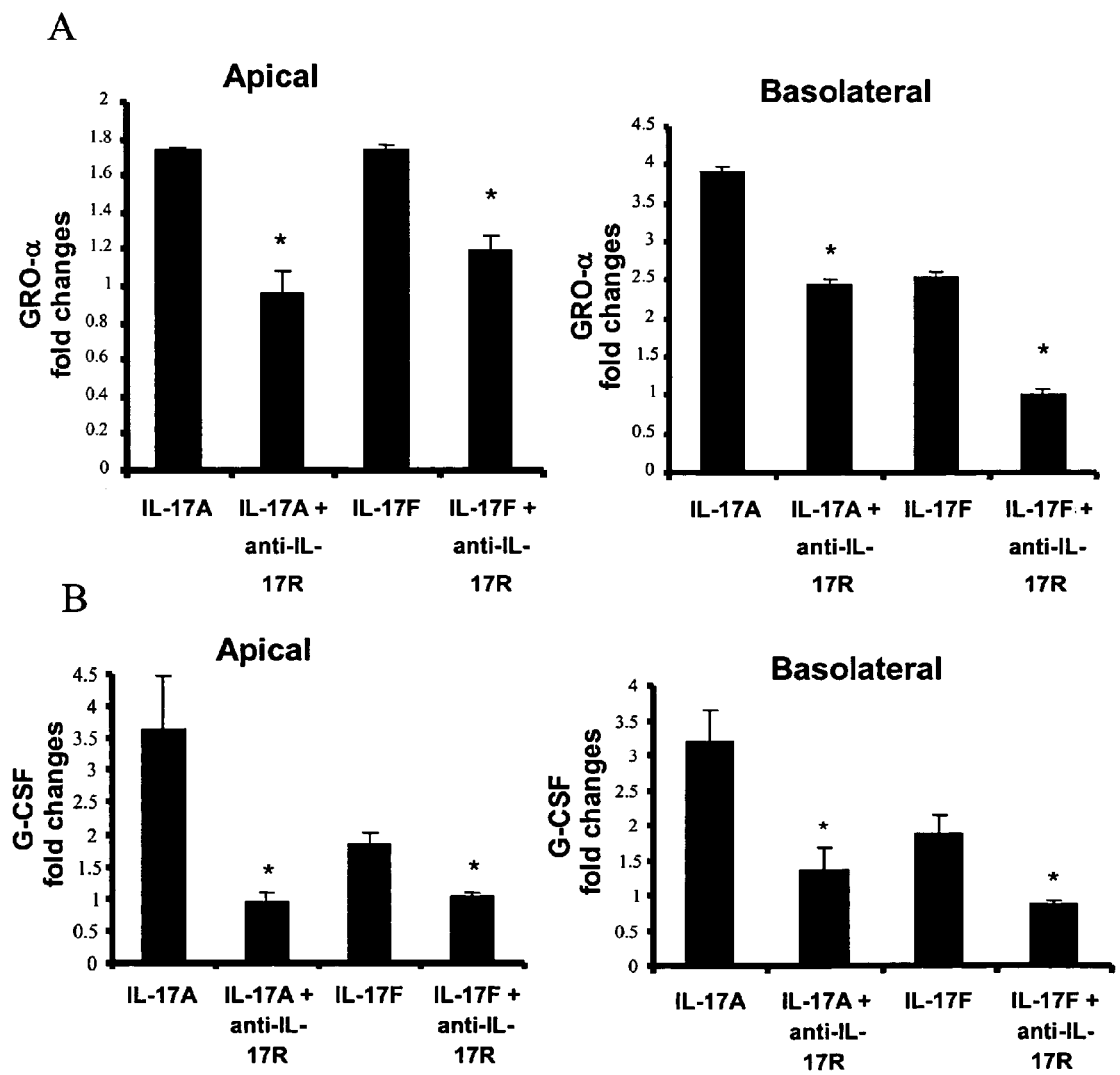
FIG. 3 shows the concentrations (fold change compared to control media; y-axis) of A) GRO-α and B) G-CSF in apical or basolateral media collected from primary HBE cells that were either pretreated with 2 μg/ml IL-17 receptor antibody (anti-IL-17R) for 30 minutes (second and fourth bars in each graph) or untreated (first and third bars) prior to 24 hour incubation with either 10 ng/ml of IL-17A or IL-17F. Results are expressed as the mean±SEM of three separate experiments (* denotes $p<0.05$ by ANOVA).

GRO-α and G-CSF Secretion Induced by IL-17A and IL-17F is Decreased by Anti-IL-17 Receptor Ab To determine polarization of GRO-α and G-CSF secretion in response to IL-17A and IL-17F, primary HBE cells were stimulated with IL-17A and IL-17F for 24 h, and GRO-α and G-CSF were assayed in apical or basolateral fluid. Both GRO-α and G-CSF were secreted both apically and basolaterally, with GRO-α showing a greater induction in basolateral secretion compared to G-CSF (FIG. 3). Preincubation with anti-IL-17R Ab significantly abrogated induction of GRO-α and G-CSF secretion mediated by both IL-17A and IL-17F in apical and basolateral media (FIG. 3). These results support the notion that the IL-17R is required for either IL-17A or IL-17F activity on HBE cells to induce G-CSF and GRO-α production.

Example 5

IL-17A and IL-17F Upregulate DEFB 104 Expression

Figure 4:
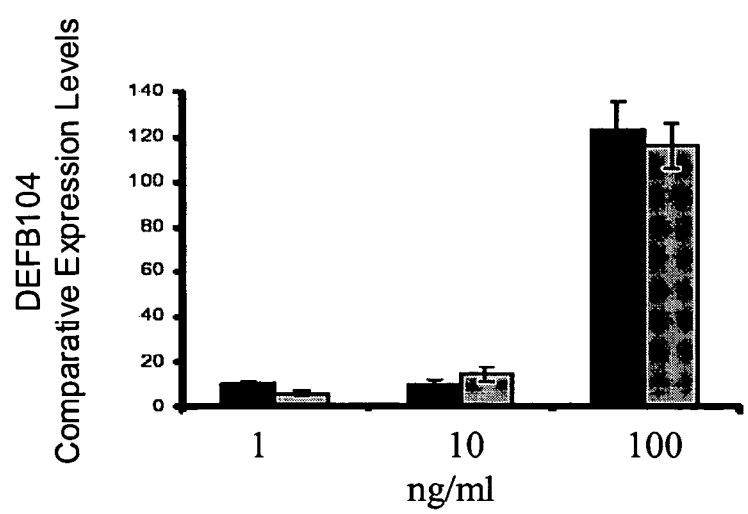
FIG. 4 shows comparative expression levels of DEFB104 (y-axis), as analyzed by Real-Time PCR, relatively quantified to 18s expression levels, and normalized with the control, and in primary HBE cells that were A) stimulated with 1 ng/ml, 10 ng/ml, or 100 ng/ml (x-axis) of IL-17A (■) or IL-17F(□) for 24 hrs., B) preincubated with anti-IL-17R antibody prior to the addition of IL-17A or IL-17F to the media, or C) incubated with IL-17A alone, IL-17F alone, TNF-α alone, or TNF-α with either IL-17A or IL-17F. Results are expressed as the mean±SEM of three separate experiments (* denotes $p<0.05$ by ANOVA).
Figure 4:
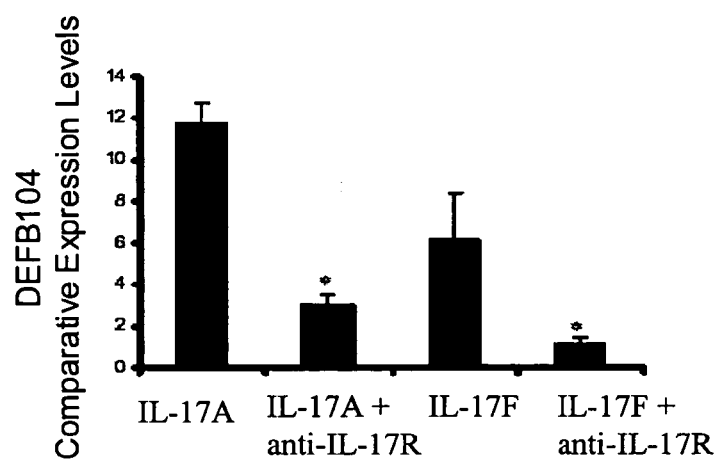
Figure 4:
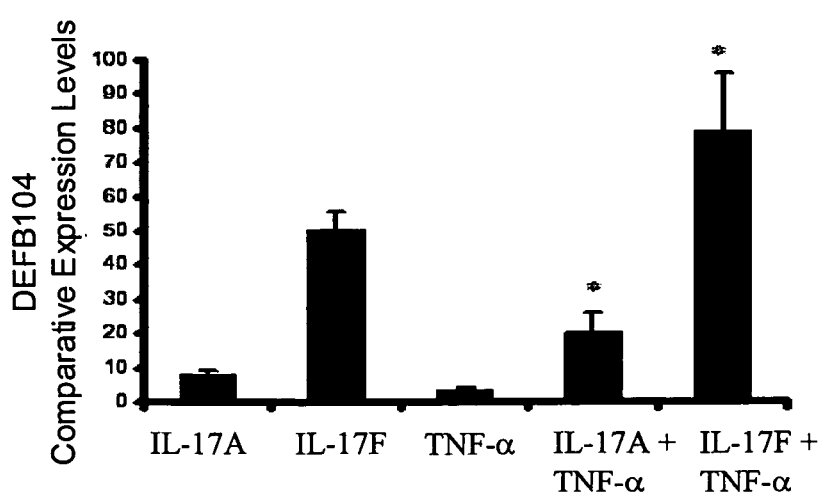

IL-17A and IL-17F (both at 10 ng/ml) were added to HBE cultures, RNA was extracted 24 h later, and human Beta defensin-4 mRNA expression (DEFB104 gene) was analyzed by real time RT-PCR and normalized to 18s ribosomal RNA. DEFB 104 was upregulated by both IL-17A and IL-17F in a dose-dependent fashion (FIG. 4A), but IL-17A had greater fold induction than IL-17F at 10 ng/ml for 24 hrs (ΔΔCT: −3.34+0.44 SEM vs. −2.23+0.31 SEM, respectively). Preincubation with 2 μg/ml anti-IL-17R antibody partially inhibited the effect of 100 ng/ml IL-17A and 100 ng/ml IL-17F by 62.5% and 77.6%, respectively, indicating that IL-17 receptor signaling is also required for DEFB104 upregulation by both cytokines (FIG. 4B). Finally, the effects of combining IL-17A (1 ng/ml) and IL-17F (10 ng/ml) with TNF-α (1 ng/ml) for DEFB 104 induction were assessed. An additive effect was found with the combination of either IL-17A and TNF-α, or IL-17F and TNF-α (FIG. 4C). The combination of both IL-17A and IL-17F also produced an additive effect on DEFB104 induction (FIG. 4C).

Example 6

IL-17 Receptor is Functionally Expressed on the Basolateral Surface of Respiratory Epithelial Cells Immunohistochemical staining for IL-17 receptor was performed on frozen sections of human lung specimens. In contrast to a control section that did not show unspecific staining, IL-17R was found expressed in respiratory epithelial cells as well as in lung parenchymal cells and localized mainly to the basolateral surface of respiratory epithelial cells (data not shown). To confirm the immunohistochemical findings, an experiment in which HBE cells were incubated with IL-17A or IL-17F in basolateral or apical media for 24 h was designed. Conditioned basolateral media for G-CSF and GRO-α was assayed, and it was found that both growth factors were upregulated when IL-17A and IL-17F were applied in basolateral media. However, no induction of GRO-α or G-CSF was observed when IL-17A or IL-17F was applied apically (FIG. 5). Taken together, these data strongly suggest that IL-17F bioactivity occurs via signaling through IL-17R on the basolateral side of HBE cells.

Example 7

TNF Receptors I and II are Structurally and Functionally Expressed on the Basolateral Surface of Respiratory Epithelial Cells TNF receptors I (TNF-RI) and II (TNF-RII) were immunohistochemically stained on polarized primary HBE cells grown on Transwell membranes using anti-human TNF-RI and anti-human TNF-RII monoclonal antibodies. Both receptors were found to be expressed in HBE cells (data not shown). As a negative control, a filter was only stained with secondary antibody, and it did not show unspecific staining (data not shown). Further more ZX-axis reconstruction showed that TNF-RI and TNF-RII localized to the lateral membranes of HBE cells, below tight junctions (data not shown).

To confirm the immunohistochemical findings, an experiment in which HBE cells were incubated with IL-17F and/or TNF-α in basolateral or apical media for 24 h was designed. Conditioned basolateral media was assayed. G-CSF was upregulated when IL-17F and/or TNF-α was applied in basolateral media but no induction of G-CSF was observed with IL-17F and/or TNF-α was applied apically (FIG. 6A). Taken together, these data suggest that signaling that leads to synergism between IL-17F and TNF-α occurs basolaterally in HBE cells.

To address the importance of the TNF receptors I and II on the signaling required for synergism between IL-17F and TNF-α, HBE cells were preincubated with either or both anti-human TNF-RI and recombinant human TNF-RII:Fc chimera. The synergistic effect on G-CSF secretion after combining IL-17F and TNF-α was blocked by anti-human TNF-RI and by recombinant TNF-RII:Fc chimera (FIG. 6B). Unexpectedly, the level of G-CSF secreted by HBE cells in response to the combination of IL-17F and TNF-α in the presence of either anti-human TNF-RI or TNF-RII:Fc chimera was lower than the level of G-CSF secreted by HBE cells in response to IL-17F stimulation (FIG. 6B), suggesting that even when IL-17F is applied alone to HBE cultures, it has a synergistic effect by interacting with TNF-α that is tonically secreted by these cells. Only incubation with TNFRII:Fc chimera reduced G-CSF secretion by HBE cells to a level approximately equivalent to the level of G-CSF secreted by HBE cells in response to IL-17A stimulation (FIG. 6C).

Example 8

IL-17A and IL-17F Levels are Increased in Cystic Fibrosis Patients Undergoing Pulmonary Exacerbation Cystic fibrosis (CF) is a lung disease characterized by persistent endobronchial infection and neutrophilic lung inflammation (Karp et al. (2004) *Nat. Immunol.* 5:388-92) and high sputum CXCL8 levels (Smountas et al. (2004) *Clin. Biochem* 37:1031-36; Sagel et al. (2001) *Am. J. Respir. Crit. Care Med.* 164:1425-31). As Ye and colleagues ((2001) *J. Exp. Med.* 194:519-527) previously showed that IL-17R signaling is critical for CXCL2 expression in murine lung in response to Gram-negative infection, it was hypothesized that IL-17A and IL-17F would be upregulated in the sputum of CF patients undergoing pulmonary exacerbation. In support of this, preliminary studies demonstrated higher IL-17A levels in patients with CF undergoing bronchoscopy for ongoing pulmonary exacerbation compared to controls with chronic cough due to asthma or gastroesophageal reflux disease (data not shown). As these samples could be subject to selection bias due to the decision to clinically perform bronchoscopy, IL-17A, IL-17F and the proximal mediator IL-23 (p19) in sputum samples from eight adult CF patients (mean age: 22) undergoing pulmonary exacerbation (requiring hospitalization and intravenous antibiotics) were elected to be investigated. On day 1 of hospitalization, increased levels of IL-17A and IL-17F were readily detectable when compared with sputum samples collected from four subjects not diagnosed with CF (59.58 pg/ml±5.22 (S.E.M.) vs. 4.17±2.13 for IL-17A; and 84.67±10.87 vs. 20.1±3.25 for IL-17F). Sputum was collected and analyzed serially during the antibiotic treatment. IL-17A and IL-17F concentrations dramatically decreased by day 20 (FIG. 7A), reaching levels similar to subjects not diagnosed with CF. A panel of 18 other cytokines in the sputum of these patients was measured using Luminex cytokine beads, and it was found that that IL-8, IL-6, G-CSF, GRO-α, MCP-1, MIP-1β, INF-α, GM-CSF and IL-1β were also increased at day 1 of hospitalization and impressively reduced by day 20 (see, e.g., FIG. 7B), showing an overall pattern similar to that seen for IL-17A and IL-17F. Similar expression patterns were seen whether cytokine/chemokine concentrations were corrected for total protein content or not. Lastly, as IL-23, a product largely of macrophages and dendritic cells, is a proximal regulator of IL-17A and IL-17F, Western blot analysis of sputum samples [obtained from three cystic fibrosis patients suffering from pulmonary exacerbation just prior to treatment with antibiotics (day 1 of hospitalization) and after 20 days of antibiotic treatment] was performed to detect the presence of IL-23 p19 protein. IL-23 was detected in all of the patients with CF undergoing pulmonary exacerbation; in two out of three patients, the level of IL-23 was higher at day 1 of hospitalization and declined by day 20 (data not shown).

Example 9

Discussion

IL-17A and IL-17F are products of activated T cells (Moseley (2003) *Cytokine Growth Factor Rev.* 14:155-74) in response to both infectious (Ye et al. (2001) *Am. J. Respir. Cell Mol. Biol.* 25:335-40) and antigenic stimuli (Hellings et al. (2003) *Am. J. Respir. Cell Mol. Biol.* 28:42-50). Lipopolysaccharide of Gram-negative bacteria appears to induce IL-17A and IL-17F through TLR4-dependent and IL-23-dependent pathways (Happel et al. (2003) *J. Immunol.* 170:4432-36; Aggarwal et al. (2003) *J. Biol. Chem.* 278: 1910-14; Linden and Adachi (2002) *Allergy* 57:769-75). Overexpression of IL-17A or IL-17F in the lung results in the induction of CXC chemokines and neutrophil recruitment (Ye et al. (2001) *Am. J. Respir. Cell Mol. Biol.* 25:335-40; Hurst et al. (2002) *J. Immunol.* 169:443-53). Deficiency of IL-17R signaling through gene targeting results in an enhanced susceptibility to Gram-negative bacterial pulmonary infections with defects both in granulopoiesis and pulmonary neutrophil recruitment (Ye et al. (2001) *J. Exp. Med.* 194:519-28). Inhibition of IL-17A also has been reported to diminish lipopolysaccharide-induced lung neutrophil recruitment (Laan et al. (1999) *J. Immunol.* 162:2347-52; Ferretti et al. (2003) *J. Immunol.* 170:2106-12.) The defect in granulopoiesis in IL-17R knockout mice is associated with a greater than 90% reduction in G-CSF release (Ye et al. (2001) *J. Exp. Med.* 194:519-28). Moreover, systemic overexpression of IL-17A results in a marked induction in granulopoiesis, which is, in part, dependent on G-CSF (Schwarzenberger et al. (1998) *J. Immunol.* 161:6383-89; Schwarzenberger et al. (2000) *J. Immunol.* 164:4783-89).

To better define the role of IL-17A and IL-17F in regulating G-CSF and the CXC chemokine GRO-α in the lung, IL-17 receptor expression in lung tissue was examined, and significant expression of IL-17R in basal respiratory epithelial cells was found. Incubation of polarized HBE cells with both IL-17A and IL-17F resulted in similar profiles of cytokine responses as measured by Bio-Plex with the induction of IL-8 and IL-6 (data not shown) in addition to G-CSF and GRO-α. It was also demonstrated that IL-17F synergizes with TNF-α to further induce G-CSF and GRO-α production by bronchial epithelial cells isolated from the human lung. In contrast to these findings, Numasaki and coworkers ((2004) *Immunol. Lett.* 95:97-104) reported that IL-17F has an inhibitory effect on TNF-α-induced secretion of G-CSF. However, the Numasaki study was performed in lung microvascular endothelial cells, which may differ in this response.

Both IL-17A and IL-17F appear to involve the IL-17 receptor in regulating GRO-α and G-CSF secretion, as a monoclonal antibody specific for the IL-17R significantly attenuated the release of these cytokines in response to IL-17A and IL-17F. However, due to low ligand efficiency with this receptor (Hymowitz et al. (2001) *EMBO J.* 20:5332-41), the possibility of coreceptors involved in IL-17F signaling cannot be excluded (Kolls and Linden (2004) *Immunity* 21:467-76). IL-17F has recently been shown in vitro to bind to IL-17RC (Kuestner et al. (2005) *Keystone Symposia: Cytokines, Disease, and Therapeutic Intervention,* 49(Abstract)). In support of these data, a soluble IL-17R was efficient in inhibiting IL-17A bioactivity but not IL-17F in HBE cells. These data suggest that binding of IL-17F is different for the cell membrane receptor, or that a coreceptor complex involving IL-17R is required for IL-17F responses. Another possibility is cross-reactivity of the mAb to IL-17RC; however this is unlikely, as homology of IL-17RC to IL-17R is only 15% (Kolls (2004) *Immunity* 21:467-76)). Moreover, the bioactivity of IL-17A, IL-17F, and TNF-α was greatest when the ligands were applied basolaterally, suggesting that functional IL-17A, IL-17F and TNF-α signaling likely occurs through the basolateral surface of airway epithelial cells. This receptor localization makes teleological sense, as a prominent potential source of IL-17A and IL-17F is activated T cells that can reside in the submucosal space (Kolls and Linden (2004) *Immunity* 21:467-76). In fact, Langrish and colleagues have recently defined a population of ThIL-17 cells that coexpress IL-17A and IL-17F as well as TNF-α (Langrish et al. (2005) *J. Exp. Med.* 201(2):233-40). Thus, ThIL-17 cells may represent a critical population of cells that interact with the human bronchial epithelium cells that mediate inflammatory responses. Using soluble TNF-α, it was demonstrated that TNF-RI is critical for synergy with IL-17A and IL-17F. However, since HBE cells also express TNF-RII, these cells may also respond to cell surface TNF expressed on ThIL-17, which preferentially binds and signals via TNF-RII (Grell et al. (1995) *Cell* 83:793-802). Of note is the fact that the concentrations used to elicit G-CSF and GRO-α responses in HBE cells (see FIG. 7) are approximately 10-100 times higher than that detected in sputum. This likely reflects the fact that local tissue concentrations in the lung may be higher than that in sputum (which is rich in proteases), or the fact that IL-17A and IL-17F may require synergistic cytokines such as TNF-α to signal at pg/ml concentration (Kolls (2004) *Immunity* 21:467-76). The mechanism of synergy of TNF-α with IL-17A and IL-17F has not been completely elucidated, but one mechanism may involve synergistic induction of transcription factors, such as C/EBPdelta, which drives subsequent gene transcription (Shen et al. (2005) *J. Leukoc. Biol.* 77:388-99).

IL-17A has been reported to be upregulated in many inflammatory autoimmune diseases including rheumatoid arthritis (Lubberts (2003) *Curr. Opin. Investig. Drugs* 4:572-77), multiple sclerosis (Lock et al. *Nat. Med.* 8:500-08), and inflammatory bowel disease (Fujino et al. (2003) *Gut* 52:65-70). It has recently been shown that T cell-derived IL-17A and IL-17F are regulated by TLR4 on macrophages and dendritic cells and subsequent IL-23 production by these cells. Moreover, IL-17A and IL-17F have a similar chromosomal location and likely arose from a gene duplication event. Based on these data, the ability of IL-17A and IL-17F to mediate lung neutrophilia (Laan et al. (1999) *J. Immunol.* 162:2347-52), and the fact that chronic inflammation in CF is predominantly neutrophilic, it is likely that IL-17A and IL-17F play roles in airway inflammation in the setting of chronic Gram-negative bacterial infections, such as bronchiectasis or cystic fibrosis (CF).

Towards this end, it was found that both IL-17A and IL-17F were elevated in the sputum of adult CF patients undergoing a pulmonary exacerbation. Moreover, elevation of IL-17A and IL-17F levels was associated with previously identified inflammatory mediators such as IL-8 (Sagel et al. (2001) *Am. J. Respir. Crit. Care Med.* 164:1425-31) and G-CSF (Schuster et al. (1995) *Eur. Arch. Otorhinolaryngol.* 252(suppl. 1):S59-S60), suggesting that these IL-17 family members may play roles in ongoing neutrophil recruitment into the airways of these patients. Furthermore, it is postulated that IL-17A and IL-17F may regulate CXC chemokine and G-CSF release in patients with CF. Additionally, IL-23p19 was detected in concentrated sputum at levels approaching 100 ng/ml, which levels are well within the range for effecting human T cell production of IL-17 (Eijnden et al. (2005) *Eur. J. Immunol.* 35:469-75).

It is believed that these data are the first to measure IL-17F in clinical samples. As chronic inflammation is thought to be critical to loss of lung function in the setting of cystic fibrosis, the data contained herein suggest that IL-17A and IL-17F are two IL-17 family members that represent excellent therapeutic targets to antagonize neutrophil-mediated inflammation. Moreover, a strategy that antagonizes IL-17R signaling may likely block both the action of IL-17A and IL-17F.

What is claimed is:

1. A method of diagnosing cystic fibrosis in a subject, comprising the steps of:
   (a) measuring a test amount of an interleukin-17F (IL-17F) gene product in a sample from a subject suspected of having cystic fibrosis;
   (b) determining a normal range of the IL-17F gene product by measuring an amount of the IL-17F gene product in multiple samples from at least one healthy subject or at least one sample from multiple healthy subjects; and
   (c) comparing the test amount with the normal range of the IL-17F gene product,
   wherein the sample from the subject suspected of having cystic fibrosis and the multiple samples from at least one healthy subject or the at least one sample from multiple healthy subjects are selected from the group consisting of sputum, tissue from airway, and bronchoalveolar lavage; and
   whereby a test amount above the normal range provides a positive indication in the diagnosis of cystic fibrosis.

2. The method of claim 1, wherein the subject is undergoing a pulmonary exacerbation.

3. The method of claim 2, wherein the pulmonary exacerbation is due to an infectious agent.

4. The method of claim 1, wherein the IL-17F gene product is an IL-17F protein.

5. The method of claim 4, wherein the IL-17F protein is detected with an anti-IL-17F antibody.

6. The method of claim 1, wherein the IL-17F gene product is an IL-17F mRNA.

7. A method of prognosing pulmonary exacerbation in a subject diagnosed with cystic fibrosis, comprising the steps of
   (a) measuring a test amount of an IL-17F gene product in a sample from the subject diagnosed with cystic fibrosis;
   (b) determining a prognostic range of the IL-17F gene product by measuring an amount of the IL-17F gene product in samples from multiple subjects with varying seventies of with cystic fibrosis undergoing pulmonary exacerbation; and
   (c) comparing the test amount with the prognostic range of the IL-17F gene product,
   wherein the sample from the subject diagnosed with cystic fibrosis and the samples from the multiple subjects with varying seventies of cystic fibrosis undergoing pulmonary exacerbation are selected from the group consisting of sputum, tissue from airway, and bronchoalveolar lavage; and
   whereby a test amount in the prognostic range indicates an increased likelihood that the subject diagnosed with cystic fibrosis will develop pulmonary exacerbation.

8. A method of monitoring the progress of pulmonary exacerbation in a subject diagnosed with cystic fibrosis, comprising the steps of
   (a) measuring a first test amount of an IL-17F gene product in a first sample from the subject diagnosed with cystic fibrosis and undergoing pulmonary exacerbation at a first time point; and
   (b) measuring a second test amount of an IL-17F gene product in a second sample from the subject diagnosed with cystic fibrosis and undergoing pulmonary exacerbation at a second time point,
   wherein the first and the second test samples are selected from the group consisting of sputum, tissue from airway, and bronchoalveolar lavage;
   wherein the second test amount below the first test amount indicates remission of pulmonary exacerbation in the subject; and
   wherein the second test amount above the first test amount indicates progression of pulmonary exacerbation in the subject.

* * * * *